United States Patent
Hoque et al.

(10) Patent No.: US 10,888,549 B2
(45) Date of Patent: Jan. 12, 2021

(54) PHARMACEUTICAL AGENTS TARGETING CANCER STEM CELLS

(71) Applicant: THE JOHNS HOPKINS UNIVERSITY, Baltimore, MD (US)

(72) Inventors: Mohammad O. Hoque, Baltimore, MD (US); David Sidransky, Baltimore, MD (US); Akira Oki, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 29 days.

(21) Appl. No.: 16/082,288

(22) PCT Filed: Mar. 7, 2017

(86) PCT No.: PCT/US2017/021073
§ 371 (c)(1),
(2) Date: Sep. 5, 2018

(87) PCT Pub. No.: WO2017/155935
PCT Pub. Date: Sep. 14, 2017

(65) Prior Publication Data
US 2019/0091202 A1   Mar. 28, 2019

Related U.S. Application Data
(60) Provisional application No. 62/304,632, filed on Mar. 7, 2016.

(51) Int. Cl.
| | | |
|---|---|---|
| *A61K 31/33* | (2006.01) | |
| *A61K 31/415* | (2006.01) | |
| *A61K 31/40* | (2006.01) | |
| *A61K 31/409* | (2006.01) | |
| *A61K 31/407* | (2006.01) | |
| *A61P 35/00* | (2006.01) | |
| *A61K 31/635* | (2006.01) | |
| *A61K 45/06* | (2006.01) | |

(52) U.S. Cl.
CPC .......... *A61K 31/415* (2013.01); *A61K 31/407* (2013.01); *A61K 31/409* (2013.01); *A61K 31/635* (2013.01); *A61K 45/06* (2013.01); *A61P 35/00* (2018.01)

(58) Field of Classification Search
CPC ....... A61K 31/33; A61K 31/415; A61K 31/40
USPC ......................................... 514/183, 406, 411
See application file for complete search history.

(56) References Cited

U.S. PATENT DOCUMENTS

| | | |
|---|---|---|
| 5,399,363 A | 3/1995 | Liversidge et al. |
| 5,466,468 A | 11/1995 | Schneider et al. |
| 5,543,158 A | 8/1996 | Gref et al. |
| 5,580,579 A | 12/1996 | Ruddy et al. |
| 5,629,001 A | 5/1997 | Michael et al. |
| 5,641,515 A | 6/1997 | Ramtoola |
| 5,725,871 A | 3/1998 | Illum |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 6,613,308 B2 | 9/2003 | Bartus et al. |
| 6,737,514 B1 | 5/2004 | Wang et al. |
| 2005/0227929 A1 | 10/2005 | Masferrer |
| 2009/0291883 A1 | 11/2009 | Wolfe et al. |
| 2014/0140149 A1 | 5/2014 | Stott et al. |
| 2018/0057594 A1 | 3/2018 | Evnin |
| 2018/0153946 A1 | 6/2018 | Alemany et al. |

FOREIGN PATENT DOCUMENTS

| | | |
|---|---|---|
| WO | 2000/038786 | 7/2000 |
| WO | 2017145162 A1 | 8/2017 |
| WO | 2017155935 A1 | 9/2017 |

OTHER PUBLICATIONS

Takenaga et al., 1998 Microparticle resins as a potential nasal drug delivery system for insulin., J Control Release 52:81-7.
Mathiowitz et al., 1997 Biologically erodable microspheres as potential oral drug delivery systems., Nature 386 (6623):410-4.
Beck et al., (2013). Unravelling cancer stem cell potential. Nat Rev Cancer 13, 727-738.
Boumahdi et al., (2014). SOX2 controls tumour initiation and cancer stem-cell functions in squamous-cell carcinoma. Nature 511, 246-250.
Brait et al., (2013). Genome-wide methylation profiling and the PI3K-AKT pathway analysis associated with smoking in urothelial cell carcinoma. Cell Cycle 12, 1058-1070.
Chakraborty et al., (2016). miRNA-regulated cancer stem cells: understanding the property and the role of miRNA in carcinogenesis. Tumour Biol.
Chan et al., (2009). Identification, molecular characterization, clinical prognosis, and therapeutic targeting of human bladder tumor-initiating cells. Proc Natl Acad Sci U S A 106, 14016-14021.
Chien et al., (2015). Lin28B/Let-7 Regulates Expression of Oct4 and Sox2 and Reprograms Oral Squamous Cell Carcinoma Cells to a Stem-like State. Cancer Res 75, 2553-2565.
Choi et al., (2014). Identification of distinct basal and luminal subtypes of muscle-invasive bladder cancer with different sensitivities to frontline chemotherapy. Cancer Cell 25, 152-165.
Coffer et al., (2004). Forkhead-box transcription factors and their role in the immune system. Nat Rev Immunol 4, 889-899.
Damrauer et al., (2014). Intrinsic subtypes of high-grade bladder cancer reflect the hallmarks of breast cancer biology. Proc Natl Acad Sci U S A 111, 3110-3115.
Eblin et al., (2007). Mitogenic signal transduction caused by monomethylarsonous acid in human bladder cells: role in arsenic-induced carcinogenesis. Toxicol Sci 95, 321-330.

(Continued)

*Primary Examiner* — Raymond J Henley, III
(74) *Attorney, Agent, or Firm* — Johns Hopkins Technology Ventures

(57) ABSTRACT

Methods for preventing or treating subjects having cancer based on the identification of pharmaceutical agents that target cancer stem cells (CSCs) have been identified. These methods include administering to the subject an effective amount of a COX2 inhibitor and an effective amount of a YAP1 inhibitor. In addition, methods of enhancing chemotherapeutic responses in cancer patients have been discovered and are described herein.

28 Claims, 24 Drawing Sheets
Specification includes a Sequence Listing.

(56) References Cited

OTHER PUBLICATIONS

Fan et al., (2013). Regulation of Hippo pathway by mitogenic growth factors via phosphoinositide 3-kinase and phosphoinositide-dependent kinase-1. Proc Natl Acad Sci U S A 110, 2569-2574.

Guerrant et al., (2016). YAP Mediates Tumorigenesis in Neurofibromatosis Type 2 by Promoting Cell Survival and Proliferation through a COX-2-EGFR Signaling Axis. Cancer Res 76, 3507-3519.

Facciabene et al., (2012). T-regulatory cells: key players in tumor immune escape and angiogenesis. Cancer Res 72, 2162-2171.

Gurner et al., (2015). Tumor PD-L1 and lymphocytic infiltrate FOXP3 status in non-muscle invasive urothelial carcinoma of bladder (NMIBC). American Urological Association, Abstract MP58-07.

Ho et al., (2012). Normal and neoplastic urothelial stem cells: getting to the root of the problem. Nat Rev Urol 9, 583-594.

Johnson et al., (2014). The two faces of Hippo: targeting the Hippo pathway for regenerative medicine and cancer treatment. Nat Rev Drug Discov 13, 63-79.

Katoh et al., (2013). CXCR2-expressing myeloid-derived suppressor cells are essential to promote colitis-associated tumorigenesis. Cancer Cell 24, 631-644.

Klein et al., (2005). Transitional cell hyperplasia and carcinomas in urinary bladders of transgenic mice with keratin 5 promoter-driven cyclooxygenase-2 overexpression. Cancer Res 65, 1808-1813.

Knowles et al., (2015). Molecular biology of bladder cancer: new insights into pathogenesis and clinical diversity. Nat Rev Cancer 15, 25-41.

Kryeziu et al., (2013). Synergistic anticancer activity of arsenic trioxide with erlotinib is based on inhibition of EGFR-mediated DNA double-strand break repair. Mol Cancer Ther 12, 1073-1084.

Kurtova et al., (2015). Blocking PGE2-induced tumour repopulation abrogates bladder cancer chemoresistance. Nature 517, 209-213.

Lee et al., (2015). Significant association of oncogene YAP1 with poor prognosis and cetuximab resistance in colorectal cancer patients. Clin Cancer Res 21, 357-364.

Lee et al., (2011). CD24(+) liver tumor-initiating cells drive self-renewal and tumor initiation through STAT3-mediated NANOG regulation. Cell Stem Cell 9, 50-63.

Letasiova et al., (2012). Bladder cancer, a review of the environmental risk factors. Environ Health 11 Suppl 1, S11.

Lian et al., (2010). The role of YAP transcription coactivator in regulating stem cell self-renewal and differentiation. Genes Dev 24, 1106-1118.

Loskog et al., (2007). Human bladder carcinoma is dominated by T-regulatory cells and Th1 inhibitory cytokines. J Urol 177, 353-358.

Michailidi et al., (2015). Involvement of epigenetics and EMT-related miRNA in arsenic-induced neoplastic transformation and their potential clinical use. Cancer Prev Res (Phila) 8, 208-221.

Moon et al., (2014). Nonsteroidal anti-inflammatory drugs suppress cancer stem cells via inhibiting PTGS2 (cyclooxygenase 2) and NOTCH/HES1 and activating PPARG in colorectal cancer. Int J Cancer 134, 519-529.

Naumov et al., (2014). CD24 knockout prevents colorectal cancer in chemically induced colon carcinogenesis and in APC(Min)/CD24 double knockout transgenic mice. Int J Cancer 135, 1048-1059.

Nishi et al., (2013). Suppression of the let-7b microRNA pathway by DNA hypermethylation in infant acute lymphoblastic leukemia with MLL gene rearrangements. Leukemia 27, 389-397.

Noh et al., (2012). Nanog signaling in cancer promotes stem-like phenotype and immune evasion. J Clin Invest 122, 4077-4093.

Overdevest et al., (2012). CD24 expression is important in male urothelial tumorigenesis and metastasis in mice and is androgen regulated. Proc Natl Acad Sci U S A 109, E3588-3596.

Pastrana et al., (2011). Eyes wide open: a critical review of sphere-formation as an assay for stem cells. Cell Stem Cell 8, 486-498.

Patrawala et al., (2005). Side population is enriched in tumorigenic, stem-like cancer cells, whereas ABCG2+ and ABCG2− cancer cells are similarly tumorigenic. Cancer Res 65, 6207-6219.

Pichler et al., (2016). Tumor-infiltrating immune cell subpopulations influence the oncologic outcome after intravesical Bacillus Calmette-Guerin therapy in bladder cancer. Oncotarget 7, 39916-39930.

Rebouissou et al., (2014). EGFR as a potential therapeutic target for a subset of muscle-invasive bladder cancers presenting a basal-like phenotype. Sci Transl Med 6, 244ra291.

Reddy et al., (2013). Regulation of Hippo signaling by EGFR-MAPK signaling through Ajuba family proteins. Dev Cell 24, 459-471.

Rothenberg et al., (2015). Inhibition of mutant EGFR in lung cancer cells triggers SOX2-FOXO6-dependent survival pathways. Elife 4.

Sabichi et al., (2011). A randomized controlled trial of celecoxib to prevent recurrence of nonmuscle-invasive bladder cancer. Cancer Prev Res (Phila) 4, 1580-1589.

Sarkar et al., (2016). Sox2 Suppresses Gastric Tumorigenesis in Mice. Cell Rep 16, 1929-1941.

Solomon et al., (2005). Cardiovascular risk associated with celecoxib in a clinical trial for colorectal adenoma prevention. N Engl J Med 352, 1071-1080.

Stolzenburg et al., (2012). Targeted silencing of the oncogenic transcription factor SOX2 in breast cancer. Nucleic Acids Res 40, 6725-6740.

Taniguchi et al., (2015). A gp130-Src-YAP module links inflammation to epithelial regeneration. Nature 519, 57-62.

Tokar et al., (2013). Chronic exposure of renal stem cells to inorganic arsenic induces a cancer phenotype. Chem Res Toxicol 26, 96-105.

Von Der Maase et al., (2005). Long-term survival results of a randomized trial comparing gemcitabine plus cisplatin, with methotrexate, vinblastine, doxorubicin, plus cisplatin in patients with bladder cancer. J Clin Oncol 23, 4602-4608.

Wang et al., (2016). Targeting YAP-Dependent MDSC Infiltration Impairs Tumor Progression. Cancer Discov 6, 80-95.

Weinstein et al., (2014). Comprehensive molecular characterization of urothelial bladder carcinoma. Nature 507, 315-322.

Wong et al., (2012). Phase II trial of cetuximab with or without paclitaxel in patients with advanced urothelial tract carcinoma. J Clin Oncol 30, 3545-3551.

Yu et al., (2007a). let-7 regulates self renewal and tumorigenicity of breast cancer cells. Cell 131, 1109-1123.

Yu et al., (2007b). Induced pluripotent stem cell lines derived from human somatic cells. Science 318, 1917-1920.

Zelenay et al., (2015). Cyclooxygenase-Dependent Tumor Growth through Evasion of Immunity. Cell 162, 1257-1270.

Zou et al., (2005). Immunosuppressive networks in the tumour environment and their therapeutic relevance. Nat Rev Cancer 5, 263-274.

Wang et al., (2010). Eicosanoids and cancer. Nat Rev Cancer 10, 181-193.

Weina et al., (2014). SOX2 and cancer: current research and its implications in the clinic. Clin Transl Med 3, 19.

Ferrario, A., et al., "Celecoxib and NS-398 Enhance Photodynamic Therapy by Increasing in vitro Apoptosis and Decreasing in vivo Inflammatory and Angiogenic Factors" Cancer Res 2005; 65: (20). Oct. 15, 2005.

Paul, A., et al., "Concurrent targeting of eicosanoid receptor 1/eicosanoid receptor 4 receptors and COX-2 induces synergistic apoptosis in Kaposi's sarcoma-associated herpesvirus and Epstein-Barr virus associated non-Hodgkin lymphoma cell lines" Translational Research 2013;161:447-468.

Wang, YX., et al., "Antiproliferative effects of selective cyclooxygenase-2 inhibitor modulated by nimotuzumab in estrogen-dependent breast cancer cells" Tumor Biol. (2012) vol. 33, pp. 957-966.

Wiwanitkit, V., "Combination of EGFR and COX-2 inhibitors in breast cancer patients" Tumor Biol. (2012) vol. 33, pp. 1261.

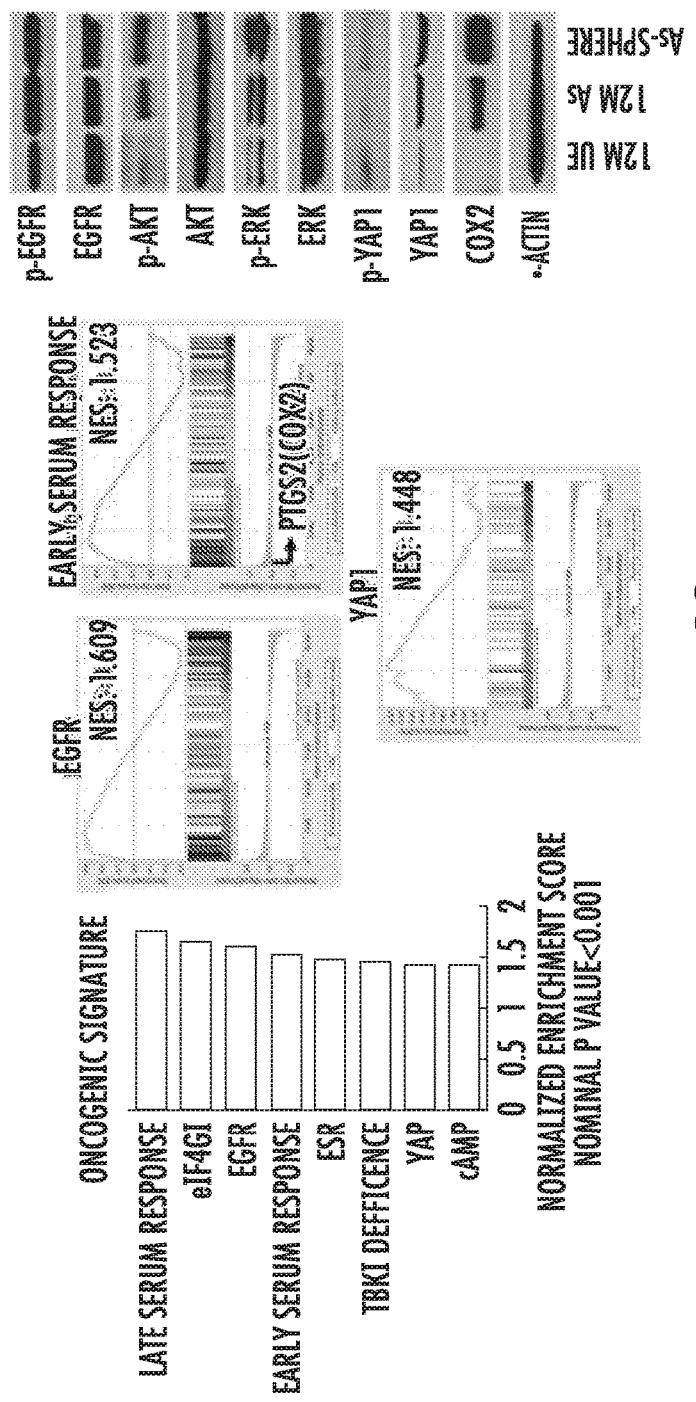
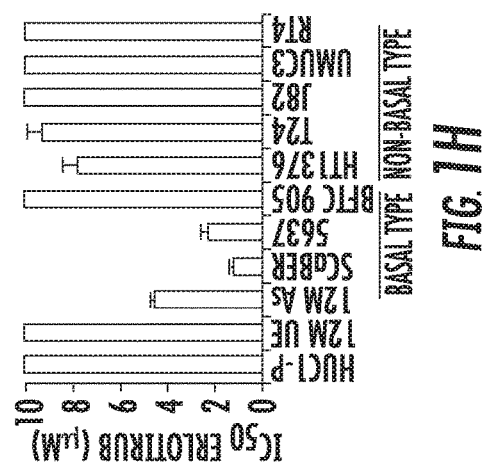
FIG. 1G
FIG. 1H

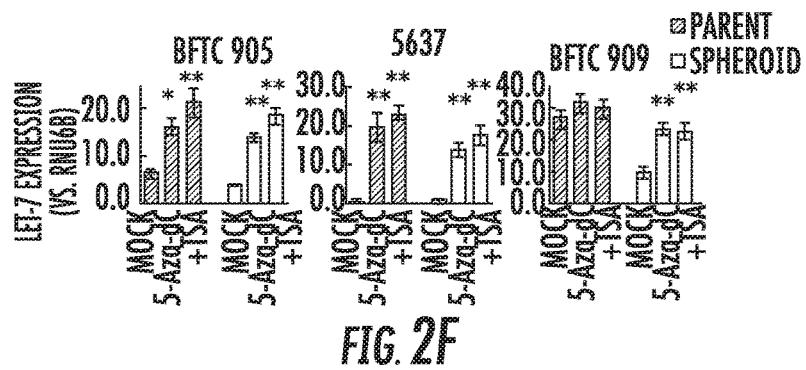
FIG. 2F
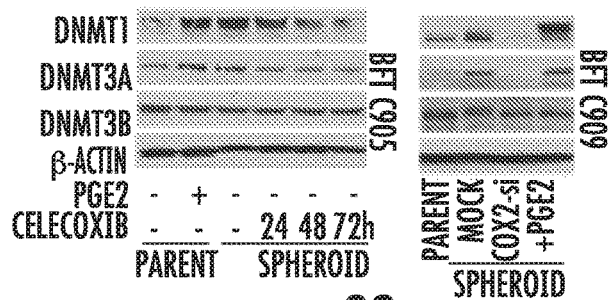
FIG. 2G
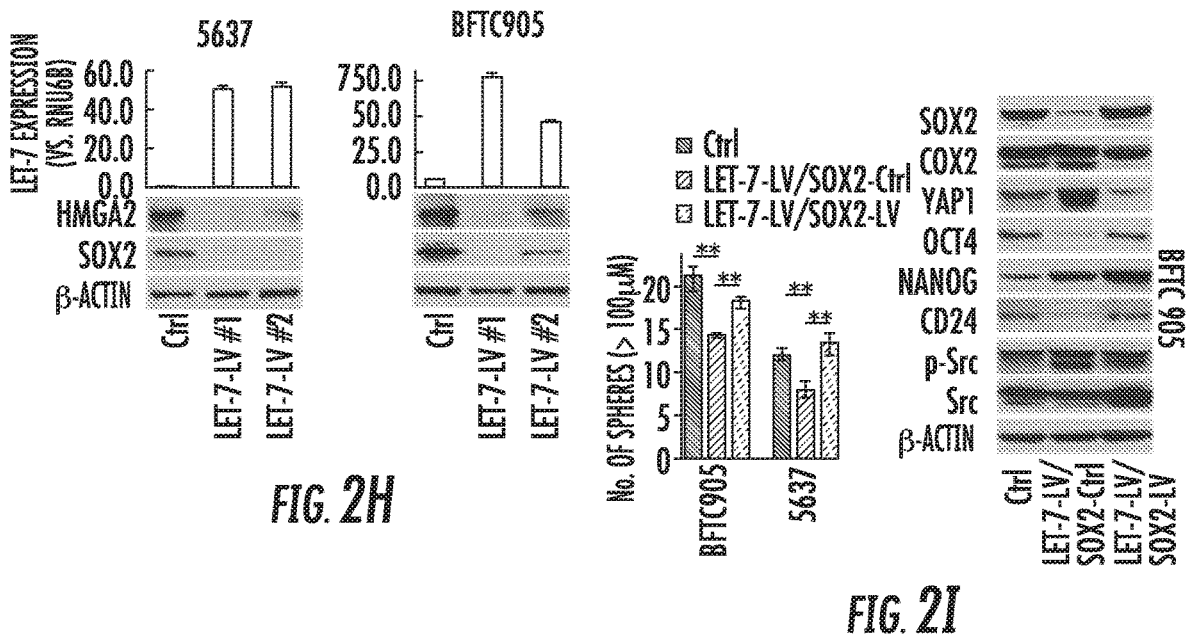
FIG. 2H
FIG. 2I

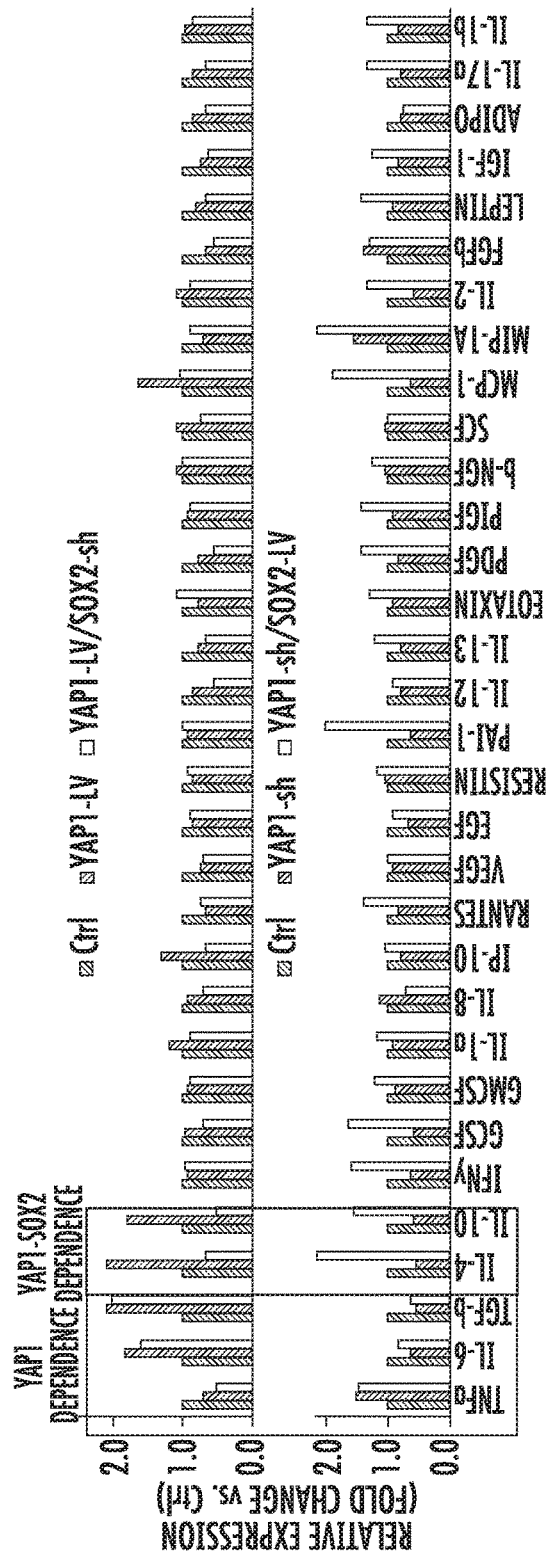
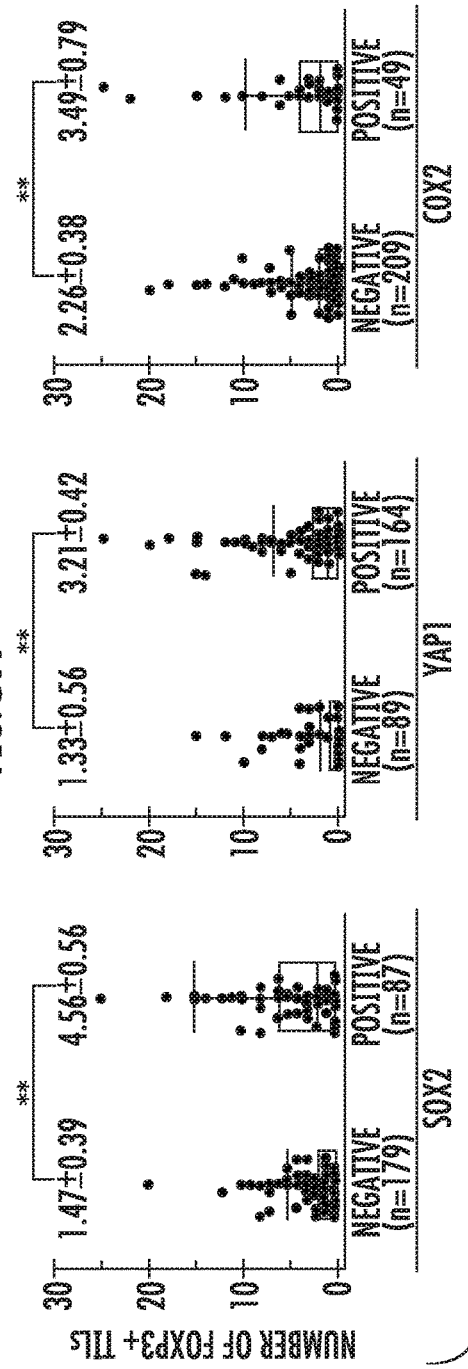
FIG. 5A
FIG. 5B

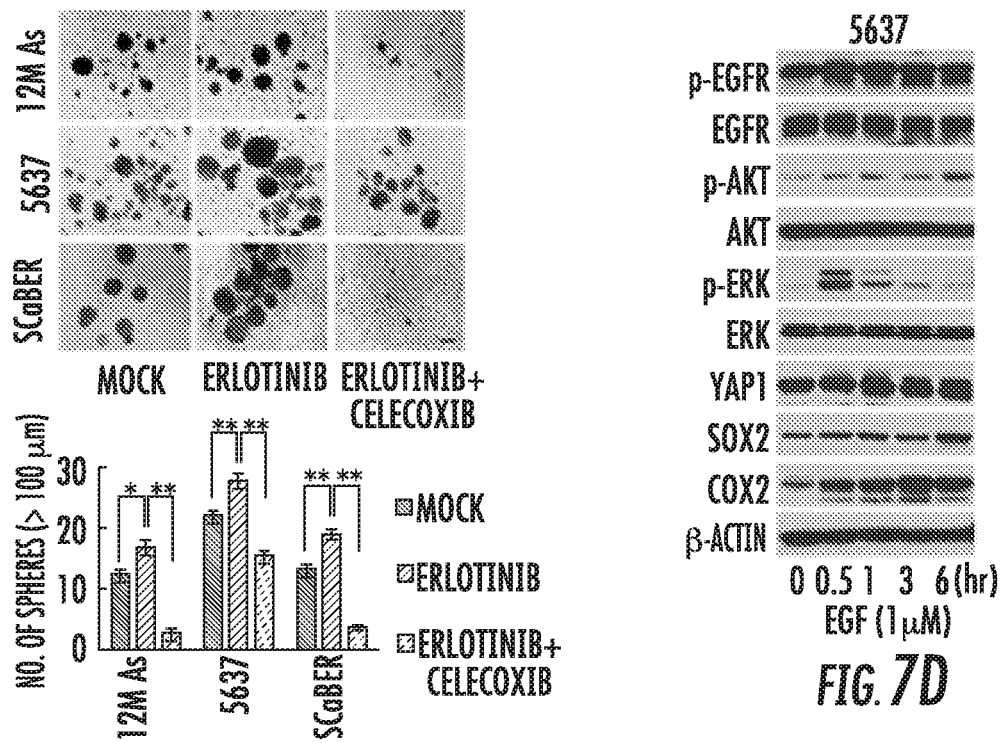
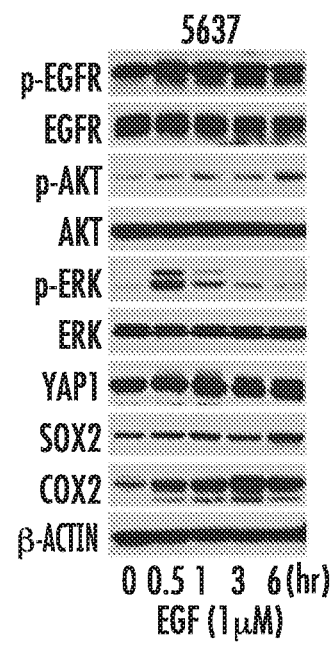
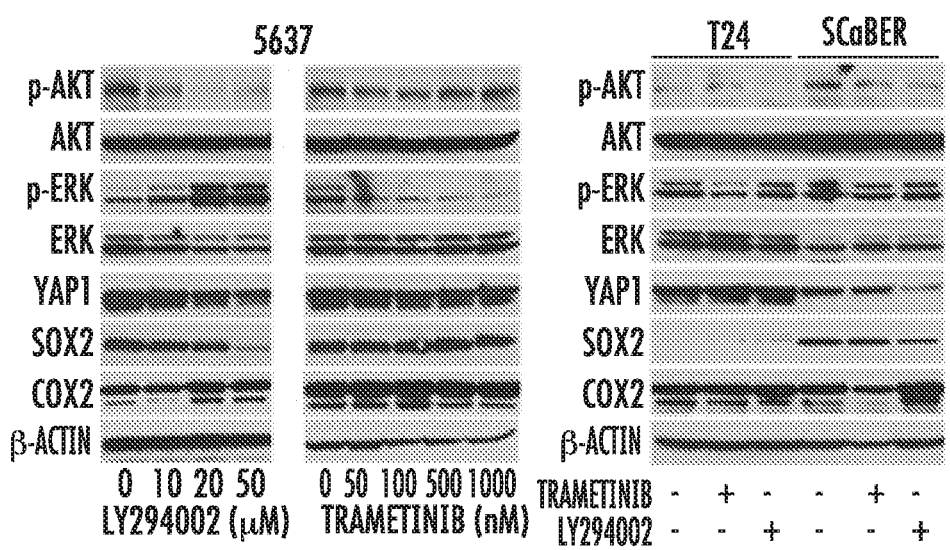
FIG. 7C
FIG. 7D
FIG. 7E

PHARMACEUTICAL AGENTS TARGETING CANCER STEM CELLS

CROSS-REFERENCE TO RELATED APPLICATIONS

This application is a 35 U.S.C. § 371 U.S. national entry of International Application PCT/US2017/021073, having an international filing date of Mar. 7, 2017, which claims the benefit of U.S. Provisional Application No. 62/304,632, filed Mar. 7, 2016, the content of each of the aforementioned applications is herein incorporated by reference in their entirety.

STATEMENT OF GOVERNMENTAL INTEREST

This invention was made with government support under grant nos. P50CA098252 and 1R01CA163594-01, awarded by the National Institutes of Health. The government has certain rights in the invention

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Feb. 28, 2017, is named P14031-02_SL.txt and is 22,259 bytes in size.

BACKGROUND OF THE INVENTION

COX-2 selective inhibitor is a form of non-steroidal anti-inflammatory drug (NSAID) that directly targets cyclooxygenase-2, COX-2, an enzyme responsible for inflammation and pain. Targeting selectivity for COX-2 reduces the risk of peptic ulceration, and is the main feature of celecoxib, rofecoxib and other members of this drug class. After several COX-2 inhibiting drugs were approved for marketing, data from clinical trials revealed that COX-2 inhibitors caused a significant increase in heart attacks and strokes, with some drugs in the class having worse risks than others. Rofecoxib (commonly known as Vioxx) was taken off the market in 2004 because of these concerns and celecoxib and traditional NSAIDs received boxed warnings on their labels.

COX-2 appears to be related to cancers and abnormal growths in the intestinal tract and have been shown to reduce the occurrence of cancers and pre-cancerous growths. The National Cancer Institute has done some studies on COX-2 and cancer and the FDA approved Celebrex for treatment of familial adenomatous polyposis (FAP). COX-2 inhibitors are currently being studied in breast cancer and appear to be beneficial. In addition, COX-2 inhibitors have also been found to be effective in suppressing inflammatory neurodegenerative pathways in mental illness, with beneficial results in trials for major depressive disorder as well as schizophrenia. The inhibition of COX-2 is paramount for the anti-inflammatory and analgesic function of the selective COX-2 inhibitor celecoxib. However, with regard to this drug's promise for the therapy of advanced cancers, it is unclear whether the inhibition of COX-2 plays a dominant role, and this has become a controversial and intensely researched issue.

YAP1 (Yes-associated protein 1), also known as YAP or YAP65, was first identified by virtue of its ability to associate with the SH3 domain of Yes and Src protein-tyrosine kinases. YAP1 is a potent oncogene, which is amplified in various human cancers, and it is one of the two main effectors of the Hippo tumor suppressor pathway. It is reported that several genes are regulated by YAP1, including Birc2, Birc5, connective tissue growth factor (CTGF), Amphiregulin (AREG), Cyr61, Hoxa1 and Hoxc13. YAP1 oncogene serves as a target for the development of new cancer drugs. Small compounds have been identified that disrupt the YAP1-TEAD complex or block the binding function of WW domains. These small molecules represent lead compounds for the development of therapies for cancer patients, who harbor amplified or overexpressed YAP oncogene.

Self-renewing bladder cancer stem/progenitor cells (CSC) contribute to tumor maintenance and resistance to therapy and accumulated evidence suggest that chronic carcinogen exposure induce "stemness" in different in vitro and in vivo models. Therapeutic targeting of CSCs in cancer patients could improve treatment response and prolong patient survival.

SUMMARY OF THE INVENTION

One embodiment of the present invention is a method for preventing or treating cancer in a subject comprising administering to the subject an effective amount of a COX 2 inhibitor and a YAP 1 inhibitor. A preferred COX 2 inhibitor is celecoxib or a pharmaceutically acceptable salt, solvate, or stereoisomer thereof. A preferred YAP1 inhibitor is verteporfin, or a pharmaceutically acceptable salt, solvate, or stereoisomer thereof. Many forms of cancer may be treated by the methods of this invention including bladder cancer and urothelial carcinoma, for example. It is preferred that a subject is administered a COX2 inhibitor and a YAP 1 inhibitor are also administered one or more other chemotherapy agents.

Another embodiment of the present invention is a method for preventing or treating cancer in a subject comprising administering to the subject an effective amount of a celecoxib, or pharmaceutically acceptable salt, solvate, or stereoisomer thereof, and an effective amount of verteporfin, or pharmaceutically acceptable salt, solvate, or stereoisomer thereof. Many forms of cancer may be treated by the methods of this invention including bladder cancer and urothelial carcinoma, for example. It is preferred that a subject is administered a COX2 inhibitor and a YAP 1 inhibitor are also administered one or more other chemotherapy agents.

Another embodiment of the present invention is a method of enhancing a chemotherapeutic response in a subject having cancer comprising the following steps: administering an effective amount of COX2 inhibitor; administering an effective amount of YAP1 inhibitor; and administering an effective amount of a chemotherapy agent. The drugs may be administered in any order. For example, a cancer patient may be administered an effective amount of COX2 inhibitor and YAP1 inhibitor prior to the administering the chemotherapy agent. Or a cancer patient may be administered an effective amount of chemotherapy agent prior to administering COX 2 inhibitor and a YAP1 inhibitor may be administered before or after the chemotherapy agent.

Another embodiment of the present invention is a method for preventing or treating cancer in a subject comprising administering to the subject an effective amount of a celecoxib or pharmaceutically acceptable salt, solvate, or stereoisomer thereof, verteporfin or pharmaceutically acceptable salt, solvate, or stereoisomer thereof and one or more chemotherapy agents.

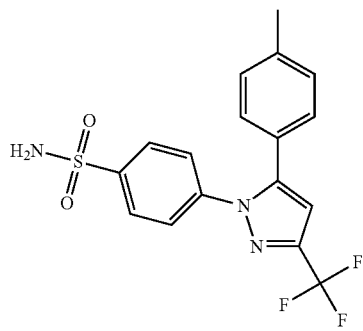 [SMILES: Cc1ccc(-c2cc(C(F)(F)F)nn2-c2ccc(S(N)(=O)=O)cc2)cc1]

Celecoxib $C_{17}H_{14}F_3N_3O_2S$

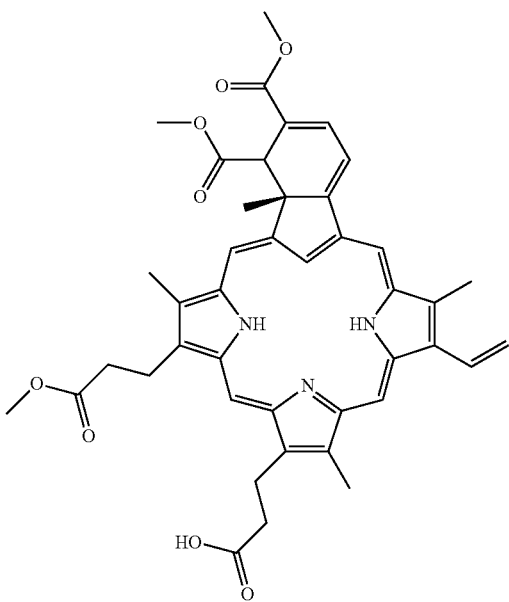 [SMILES: C=Cc1c(C)c2cc3cc(cc4[nH]c(cc5nc(cc1[nH]2)C(C)=C5CCC(=O)O)c(CCC(=O)OC)c4C)[C@@]1(C)C3=CC=C(C(=O)OC)C1C(=O)OC]

Verteporfin 3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.1$^{3,6}$.1$^{8,11}$.1$^{13,16}$.0$^{19,24}$]octacosa-1,3,5,7,9,11(27),12,14,16,18(25),19,21-dodecaen-9-yl]propanoic acid Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "activity" refers to the ability of a gene to perform its function such as COX 2 (a cyclooxygenase) responsible for the formation of prostanoids, for example.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "COX" is meant a prostaglandin-endoperoxide synthase (PTGS), and enzyme, specifically a family of isozymes responsible for the formation of prostanoids. "COX-2" is an isozyme.

By "disease" is meant any condition or disorder that damages or interferes with the normal function of a cell, tissue, or organ. Examples of diseases include cancer.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "EGFR" is meant epidermal growth factor receptor. Inhibitors of EGFR include gefitinib, erlotinib, lapatinib, cetuximab, panitumumab, vandetanib, necitumumab, and osimertinib, as examples By "EP4" is meant a prostaglandin E2 receptor 4 that is a prostaglandin receptor for prostaglandin E2 (PGE2) encoded by the PTGER4 gene in humans.

The term "express" refers to the ability of a gene to express the gene product including for example its corresponding mRNA or protein sequence (s).

The term, "obtaining" as in "obtaining an agent" includes synthesizing, purchasing, or otherwise acquiring the agent.

By "reduces" is meant a negative alteration of at least 10%, 25%, 50%, 75%, or 100%.

A "reference" refers to a standard or control conditions such as a sample (human cells) or a subject that is a free, or substantially free, of an agent such as one or more inhibitors of COX 2 and YAP 1.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "SOX2" is meant SRY (sex determining region Y)-box 2 a transcription factor that is essential for maintain self-renewal, or pluripotency, of undifferentiated embryonic stem cells. SOX2 is a member of the SOX family of transcription factors.

By "YAP1" is meant yes-associated protein 1, also known as YAP or YAP65, a protein that acts as a transcriptional regulator by activating the transcription of genes involved in cell proliferation and suppressing apoptotic genes.

BRIEF DESCRIPTION OF THE DRAWINGS

FIG. 1A-1H: Role of SOX2 in urothelial CSCs generation and maintenance. (A) Sphere formation and self-renewal assay in chronic arsenic exposed (As)-HUC1 cells for 6 to 12 months (6M As- to 12M As-cells) compared with the passage-matched unexposed (UE)-cells. Left: representative images of spheres according to different time periods of arsenic exposure (scale bars, 200 µm); Middle: the number of spheres over 100 µm; Right: the number of spheroid cells after second (P2) and third (P3) passage in self-renewal assay. Data are from 3 independent experiments. BFTC 905 and 909 cell lines, established from arsenic exposed UCB subjects, were used as a control. (B) Relative expression of stem cell-related genes using stem cell-specific RT-PCR array in parental or spheroid cells exposed at different time periods of arsenic compared with the corresponding UE-cells. Left: heat map of stem cell-specific RT-PCR array; Right: western blotting of stem cell- and EMT-related molecules. (C) Box plots of SOX2 expression measured by quantitative reverse transcriptase polymerase chain reaction (Q-RT-PCR) in urine from arsenic exposed (As; n=91) and un-exposed (n=90) normal subjects and from UCB (n=56) and normal subjects without arsenic exposure (n=108). (D) SOX2 expression in parental and spheroid bladder cancer cells compared with normal urothelial HUC1 cells, measured by western blotting. (E) In vivo tumorigenicity of stable BFTC 905 SOX2-sh cells. Upper: tumor growth curve after xenotransplantation (four mice per each group). A remarkable reduction of tumor volume was observed in SOX2-sh cells compared with parental or SOX2-Ctrl cells; Lower: tumor initiation frequency of serially diluted spheroid cells (F) In vivo tumorigenicity of stable T24 SOX2-LV cells. Upper: tumor growth curve after xenotransplantation (four mice per each group). Aggressive effect on tumorigenesis were observed in SOX2-LV cells; Lower: tumor initiation frequency of serially diluted cells. (G) Gene set enrichment analyses (GSEA) related to the oncogenic signatures on UE-cells, As-cells, and BFTC 905 cells established from arsenic exposed subjects. Left: enhanced oncogenic pathways, determined by normalized enrichment score (NES); Middle: Enrichment of EGFR, YAP1, and early serum response (ESR) gene signature. PTGS2 (encoding COX2) was top rank of metric scores within leading edge in ESR signature. Right: western blotting of EGFR pathway, YAP1, and COX2. (H) The half maximal inhibitory concentration ($IC_{50}$) value of EGFR inhibitor erlotinib treatment of 12M As, 12M UE, and bladder cancer cell lines with basal type or non-basal type. $IC_{50}$ value was calculated by exposure with the various concentration of arsenic for 72 hours using MTT assay.

Figure 1A:
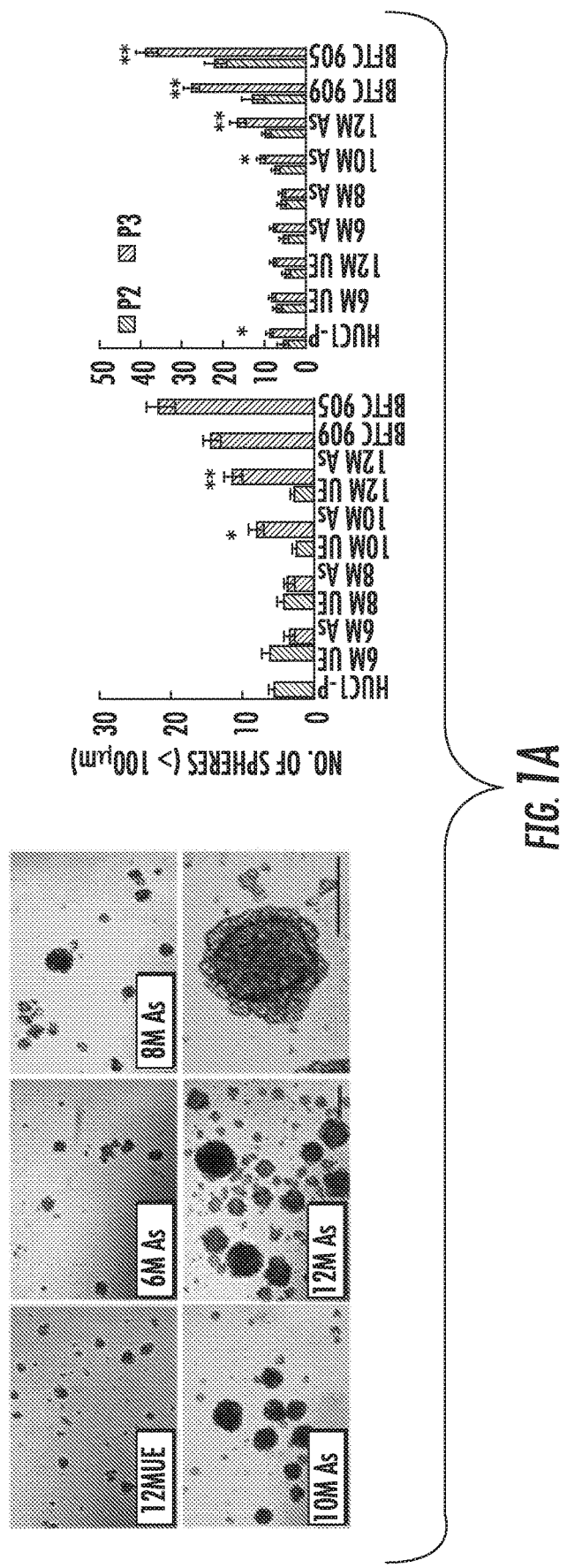

Error bars indicate mean±SEM. * P<0.05, ** P<0.01 (Wilcoxon-Mann-Whitney test (A and upper of E-F), Fisher's exact test (lower of E-F), and ANOVA with Tukey's post hoc test (C)). See also FIG. S1-S6.

FIG. 2A-2I: COX2/PGE2/let-7 signaling axis regulating SOX2 expression. (A) Left: Western blotting after celecoxib treatment for 72 hours with or without addition of PGE2 for last 24 hours. Right: Western blotting with and without 10 µM celecoxib treatment for 72 hours. (B) Left: Western blot of indicated molecules after blockade of COX2 by siRNA. Right: Bar graph of spheres after indicated treatment. Data are from 3 independent experiments. (C) Western blotting analysis (left) and sphere formation assay (right) after COX2 knockdown in SOX2-LV or SOX2-Ctrl (COX2-si/SOX2-Ctrl and COX2-si/SOX2-LV) cells. (D) Expression level of let-7 in several parental or spheroid bladder cancer cells. Upper: relative expression of let-7 after treatment with 10 µM celecoxib for 72 hours±2 µM PGE2 for 24 hours, measured by Q-RT-PCR; Lower: expression level of let-7 and methylation status of let-7 host gene MIRLET7BHG promoter, determined by bisulfite sequencing. An inverse relationship between promoter methylation of the let-7 host gene and let-7 expression was observed. (E) Methylation status of MIIRLET7BHG promoter after treatment with 10 µM celecoxib, 2 µM PGE2, or 5 µM 5-Aza-dC for 5 days in BFTC 909 cells. Upper: schematic diagram of CpG islands (red square) in the 5'-flanking region of the MIRLET7BHG promoter (SEQ ID NO: 97); Lower: Chromatogram of methylation status in the dinucleotide CpG within the promoter region by bisulfite sequencing. Red and black arrows indicate methylated and demethylated dinucleotide CpGs within the promoter region, respectively. (F) Reactivation of let-7 after treatment with 5-Aza-dC±Trichostatin A (TSA). The 5-Aza-dC led to restoration of let-7 expression. In addition, combined treatment with 5-Aza-dC and TSA upregulated the expression to a greater extent than treatment with 5-Aza-dC alone, indicating histone deacetylation may be also included in the regulatory mechanism. (G) Western blotting of DNMTs after pharmacological (left) and genetic (right) inhibition of COX2. DNMT 1 and 3A were upregulated in spheroid and PGE2-treated cells and downregulated by COX2 inhibition. (H) Expression levels of SOX2 and HMGA2 in cells transduced with let-7 lentivirus (let-7-LV). Upper: Q-RT-PCR analysis of let-7 expression; Lower: western blotting. (I) Sphere formation assay (left) and western blotting (right) after dual induction of let-7-LV and SOX2-LV (let-7-LV/SOX2-LV). Each error bar indicates mean±SEM. * P<0.05, ** P<0.01 (Wilcoxon-Mann-Whitney test (F) and Kruskal-Wallis with post-hoc test (B, C, D, and I)). See also FIG. S7.

FIG. 3A-3H: YAP1-SOX2 signaling axis in urothelial CSCs. (A) Western blotting in YAP1-knockdown (YAP1-sh) cells. Knockdown of YAP1 reduced expression of SOX2 and other stem cell-related factors (OCT4 and NANOG), whereas expression of COX2 was increased. (B) Relative expression of SOX2 72 hours after transfection with COX2 siRNA in YAP1-sh cells. Dual inhibition of COX2 and YAP1 significantly repressed SOX2 expression compared with either inhibition alone. (C) Sphere formation assay in YAP1-sh cells transfected with COX2 siRNA. Data are from 3 independent experiments. (D) In vivo tumorigenicity of stable YAP1-sh cells in the presence or absence of celecoxib treatment (four mice per each group). (E) Sphere formation assay (upper) and western blotting (lower) in BFTC 905 YAP1-sh or YAP1-Ctrl cells transduced with SOX2-sh or SOX2-Ctrl (YAP1-Ctrl/SOX2-Ctrl, YAP1-sh/SOX2-LV, and YAP1-sh/SOX2-Ctrl). Data are from 3 independent experiments. (F) Sphere formation and self-renewal assays (upper) and western blotting (lower) in BFTC 909 YAP1-LV or YAP1-Ctrl cells transduced with SOX2-LV or SOX2-Ctrl (YAP1-Ctrl/SOX2-Ctrl, YAP1-LV/SOX2-sh, and YAP1-LV/SOX2-Ctrl). (G) In vivo tumorigenic effect of SOX2 knockdown in stable YAP1 overexpressing cells (YAP1-LV/SOX2-sh). Four mice per each group. (H) In vivo tumorigenic effect of SOX2 in YAP1 and COX2 silenced cells. Left: mice injected with stable YAP1-sh/SOX2-LV cells were treated with celecoxib (five per each group); Right: tumor initiation frequency of diluted spheroid cells (100 cells/each injection). After injection of cells, mice were treated with mock or celecoxib (twelve per each group). Each error bar indicates mean±SEM. * P<0.05, ** P<0.01 (Wilcoxon-Mann-Whitney test (D) and Kruskal-Wallis with post-hoc test (B, C, E, F, G, and H)). See also FIG. S8.

Figure 4A:
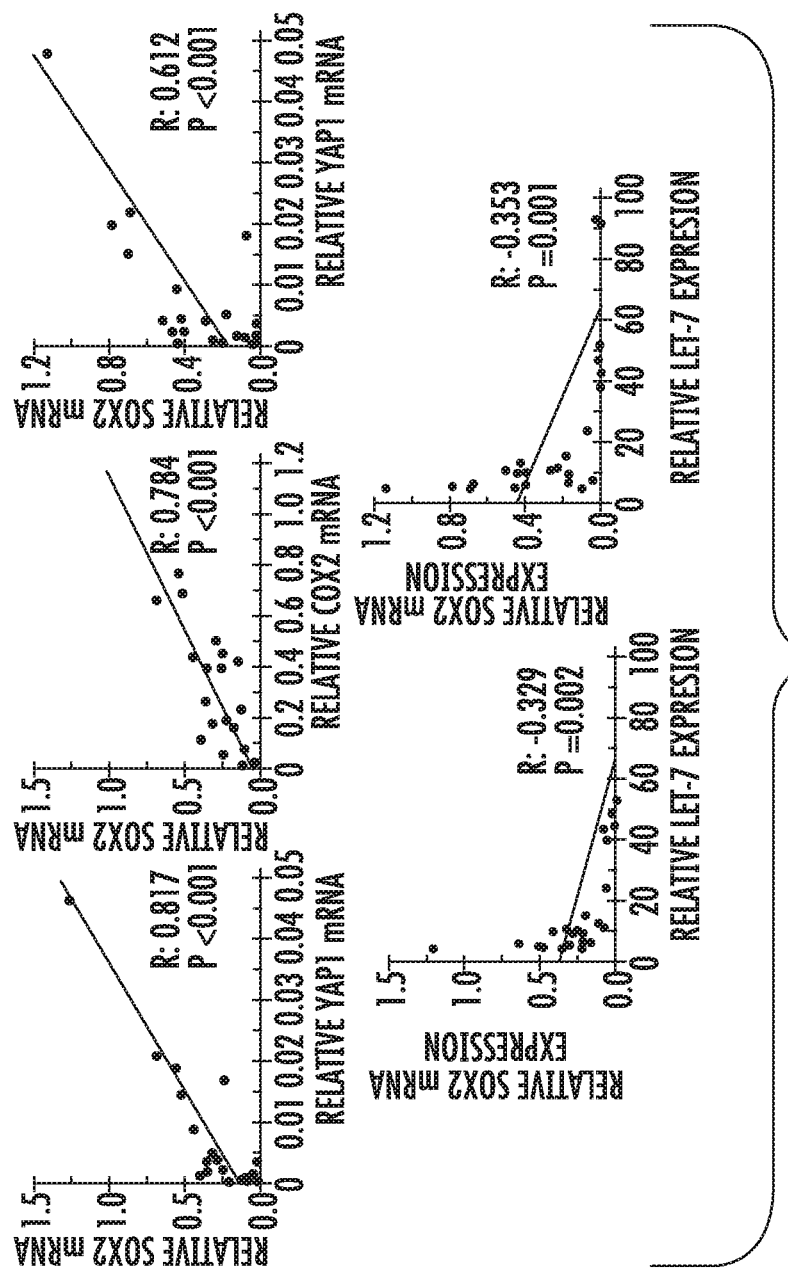
Figure 4B:
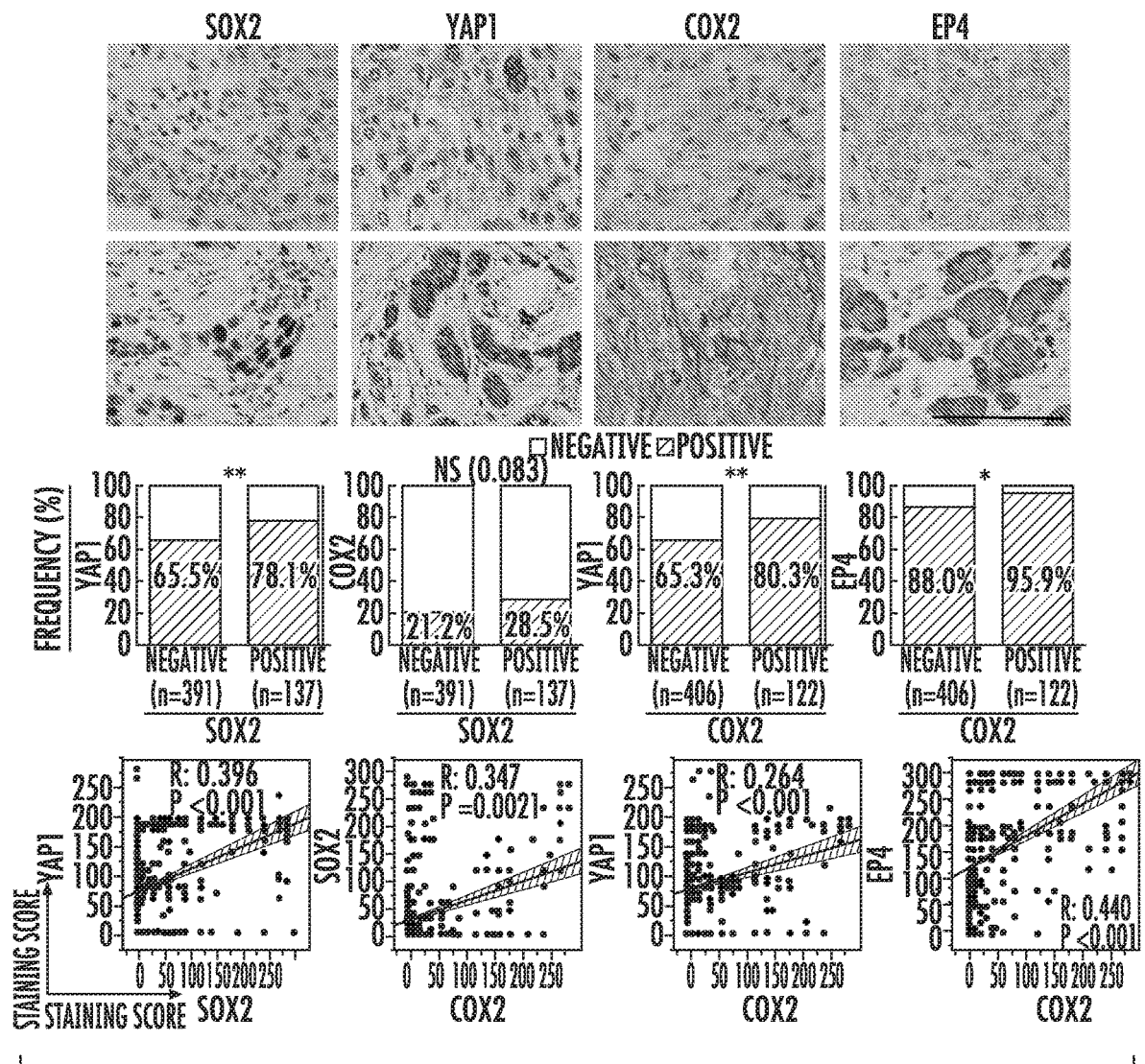

FIG. 4A-4B: Correlation between YAP1, COX2, let-7, and SOX2. (A) Linear correlation analysis of mRNA expression of SOX2, YAP1, let-7, and COX2, measured by Q-RT-PCR, in 26 primary tumor tissues. The extent of the correlation is indicated by R-coefficient. (B) Immunohistochemistry analysis in 528 primary tumor core tissues. Upper, representative images (scale bar, 500 µm); Middle, correlation between YAP1, COX2, SOX2, and EP4. * P<0.05, ** P<0.01 (the chi-square test); Lower, Linear correlation between staining scores of YAP1, COX2, SOX2, and EP4. See also FIG. S9.

Figure 5C:
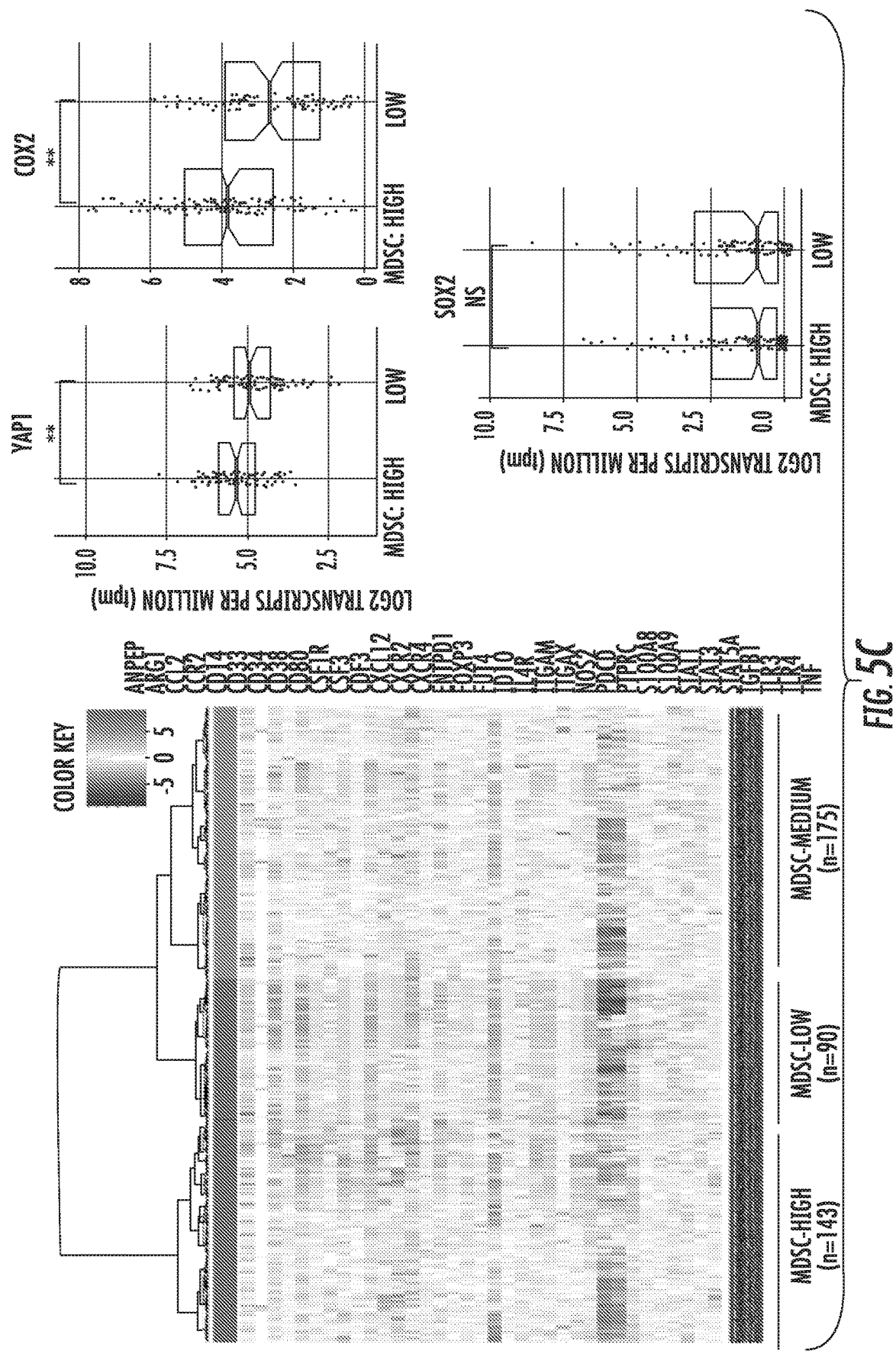

FIG. 5A-5C: Correlation between immunosuppression and YAP1, COX2, or SOX2 expression. (A) Comprehensive cytokine ELISA array in YAP1-LV, YAP-LV/SOX2-sh, YAP-sh, YAP-sh/SOX2-LV cells. (B) Box plots of the number of FOXP3-positive tumor-infiltrating lymphocytes (TILs) according to SOX2, YAP1, or COX2 expression within each tumor region, using the same field of view in primary UCB tissue microarray (TMA). FOXP3-positive TILs were counted as a number per high power filed (HPF). The two-tailed student's t-test was performed. (C) Expression of YAP1, COX2, or SOX2 in TCGA UCB samples classified as the MDSC-high groups. Left: Clustering analysis of TCGA UCB samples using 35 MDSC-related genes. Right: Expression levels of YAP1, COX2, or SOX2 in MDSC-high group. Wilcoxon ranked test was performed. Each error bar indicates mean±SEM. * P<0.05, ** P<0.01; NS, not significant. See also FIG. S9.

FIG. 6A-6F: CSC properties abrogated by combined inhibitors of YAP1 and COX2. (A) Expression level of SOX2 72 hours after combination treatment, measured by western blotting in BFTC 905 cells (left) and flow cytometry in BFTC 909 cells (right). Cells were treated with 1 µM verteporfin (VP) and/or 10 µM celecoxib for 72 hours. (B-C) In vivo therapeutic efficacy of combination treatment in BFTC 905 (B) and T24 SOX2-LV (C) tumor xenograft. Growth curves were calculated by comparing the tumor size before any treatment with size at different time point of therapy. (D) Sphere formation assay after CDDP chemotherapy combined with VP and/or celecoxib treatment for 72 hours. Upper: representative images of sphere formation (Scale bars, 200 µm). Lower: number of spheres in noted cell lines. (E) In vivo therapeutic efficacy of GC chemotherapy combined with VP and/or celecoxib (five per each group). Upper: tumor growth curve. Schedule of GC treatment was highlighted in black (GEM) and red (CDDP) arrows. Growth curves were calculated by comparing the tumor size before any treatment with size at different time point of therapy. Lower: xenograft tumor tissues were analyzed by western blotting. (F) In vivo therapeutic efficacy of GC chemotherapy combined with VP and celecoxib in PDX models (five per each group). Each error bar indicates mean±SEM. NS, not significant; * P<0.05, ** P<0.01 (Kruskal-Wallis with post-hoc test (B, C, D, E, and F)). See also FIG. S10.

FIG. 7A-7H: Acquired resistance to EGFR inhibitor due to activation of YAP1 and COX2 signaling in basal-type UCB. (A) Sphere formation assay after 1 µM erlotinib treatment for 72 hours. (B) Dynamics of SOX2, COX2, and YAP1 expression after treatment with 1 µM erlotinib with or without 10 µM celecoxib in basal-type 5637 (left and middle) and non-basal-type cells (right). In non-basal-type cells, erlotinib treatment did not affect levels of YAP1 or COX2 expression. Erlotinib continuously decreased YAP1 expression along with suppressed activation of AKT and extracellular signal-related kinase (ERK). (C) Sphere formation assay after 1 µM erlotinib±10 µM celecoxib for 72 hours. Upper: representative images (scale bars, 200 µm); Lower: the number of spheres. Data are from 3 independent experiments. (D) Western blotting after treatment with EGF. (E) Western blotting after treatment with PI3K inhibitor LY294002 (left) and MAPK/ERK1/2 inhibitor trametinib (middle) for 24 hours in basal-type 5637 cells, and 20 µM LY294002 or 100 nM trametinib in non-basal-type T24 and basal-type SCaBER cells (right). (F) In vivo therapeutic efficacy of triple blockade of EGFR, COX2, and YAP1 in basal-type cells-derived xenograft tumors. Growth curves were calculated by comparing the tumor size before any treatment with size at different time point of therapy. (G) Western blotting in xenograft tumors that acquired resistance to erlotinib (5637 cells). To further understand the mechanisms underlying acquired resistance to the EGFR inhibitor, tumors resistant to erlotinib were established by consecutively passaging tumors from mice treated with erlotinib and celecoxib. (H) In vivo therapeutic efficacy of triple blockade of EGFR, COX2, and YAP1 in tumors with acquired resistance that were established.

Each error bar indicates mean±SEM. * $P<0.05$, ** $P<0.01$ (Wilcoxon-Mann-Whitney test (A) and Kruskal-Wallis with post-hoc test (C, F, and H)).

Figure 8:
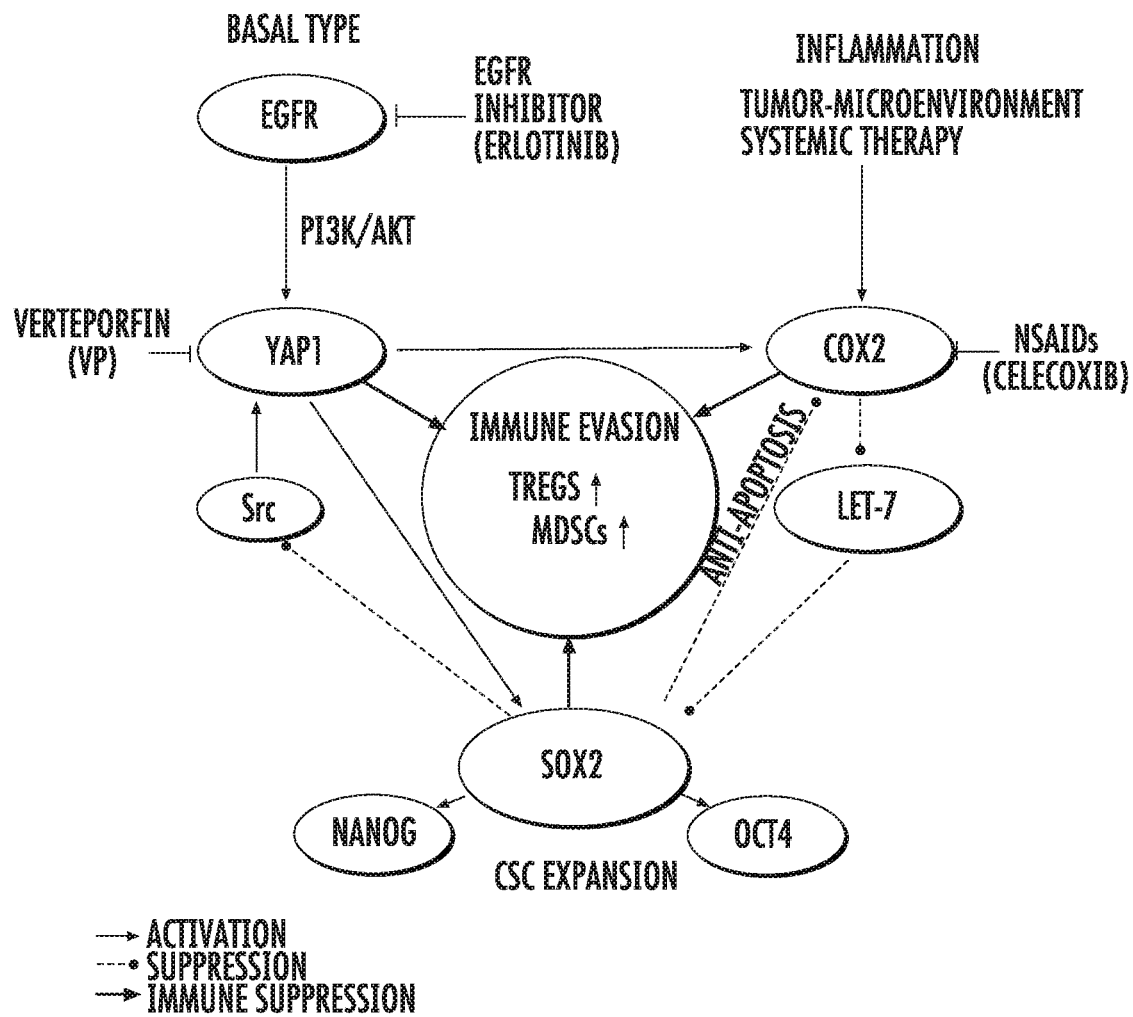

FIG. 8: Schematic representation of COX2/PGE2-let-7-SOX2 and YAP1-SOX2 axes in bladder cancer. COX2/PGE2 and YAP1 signaling pathways are required to accelerate SOX2 and mutually compensate via a negative feedback mechanism of SOX2. In basal-type, the YAP1-SOX2 axis is regulated by the EGFR pathway via PI3K/AKT signaling but is enhanced via PI3K/AKT signaling re-activated by oncogenic bypass when acquired resistance to EGFR inhibitor. Moreover, all these molecules are associated with immunosuppression. NSAIDs, nonsteroidal anti-inflammatory drugs; Tregs, regulatory T-cells; MDSCs, myeloid-derived suppressor cells.

DETAILED DESCRIPTION OF THE INVENTION

CSCs have been shown to contribute to tumorigenesis and resistance to systemic therapy, but the mechanisms of urothelial CSC expansion and applicable strategies for overcoming therapeutic resistance remain fully elusive. COX2/PGE2 and YAP1 signaling pathways mutually compensate to regulate urothelial CSCs via SOX2 and that activation of these pathways hampers the efficacy of systemic therapy by expanding CSC. Concurrent inhibition of these signaling pathways with systemic therapy elicits a robust therapeutic response by eradicating both the tumor bulk and the urothelial CSC pool. The present invention provides methods to concurrently target these pathways with systemic therapy as an effective therapeutic strategy for cancer such as bladder cancer.

Urothelial carcinoma of bladder (UCB) is the most common malignancy of the urinary system. Although 70% of newly diagnosed patients have non-muscle-invasive bladder cancer, the recurrence rate is high, and 10-30% will progress to a muscle-invasive bladder cancer (MIBC) (1). MIBC can be stratified into three subtypes with unique molecular and clinical features (basal, luminal, and p53-like types). Although UCB is chemosensitive, the prognosis of patients with metastatic disease remains poor. Basal-type UCB is sensitive to epidermal growth factor receptor (EGFR)-targeted therapy, but the mechanisms underlying acquired resistance remain elusive.

Cancer stem cells (CSCs) are relatively rare population and contribute to tumorigenesis and metastasis via specific signaling pathways that are related to stemness properties. CSCs are resistant to conventional chemotherapies that efficiently eliminate bulk tumor cells and are responsible for subsequent tumor progression or recurrence, resulting in clinical treatment failure. Thus, the elimination of CSCs is indispensable in treating malignant diseases.

Sex-determining region Y [SRY]-box 2 (SOX2), Yes-associated protein1 (YAP1) and the inflammatory enzyme cyclooxygenase 2 (COX2) are reported to be associated with numerous cancer types. SOX2 is a key transcription factor that maintains pluripotency and self-renewal in embryonic stem cells and generates induced pluripotent stem cells (iPSCs). SOX2 plays a crucial role in maintaining CSCs in several types of cancer and establishes a continuum between tumor initiation and progression via direct regulation of key genes controlling malignant stemness, survival, proliferation, and invasion. However, the biological roles and mechanisms underlying the regulation of SOX2 in UCB remain unclear. YAP1, a downstream transcriptional effector of the Hippo pathway, contributes to stemness and chemotherapy resistance. The COX2/COX2-derived prostaglandin E2 (PGE2) pathway plays a key role in tumor-promoting inflammation, a hallmark of tumor progression. Notably, chemotherapy-induced apoptotic cells release PGE2 as an inflammatory response, which in turn promotes CSC expansion. However, it is unclear how COX2/PGE2 signaling induces CSC expansion.

Environmental risk factors, such as tobacco-related carcinogens and arsenic, cause chronic inflammation and have been linked to increased UCB incidence. The inventors previously developed an in vitro stepwise model for urothelial malignant transformation by exposing the cells to cigarette smoke or arsenic in a normal urothelial cells line (HUC1), which may reveal the intimate connections between carcinogenesis, chronic inflammation, and CSCs, and provide clues to develop novel therapeutic strategies.

SOX2 is a Critical Oncogene Closely Linked with Malignant Stemness Properties

Figure 1B:
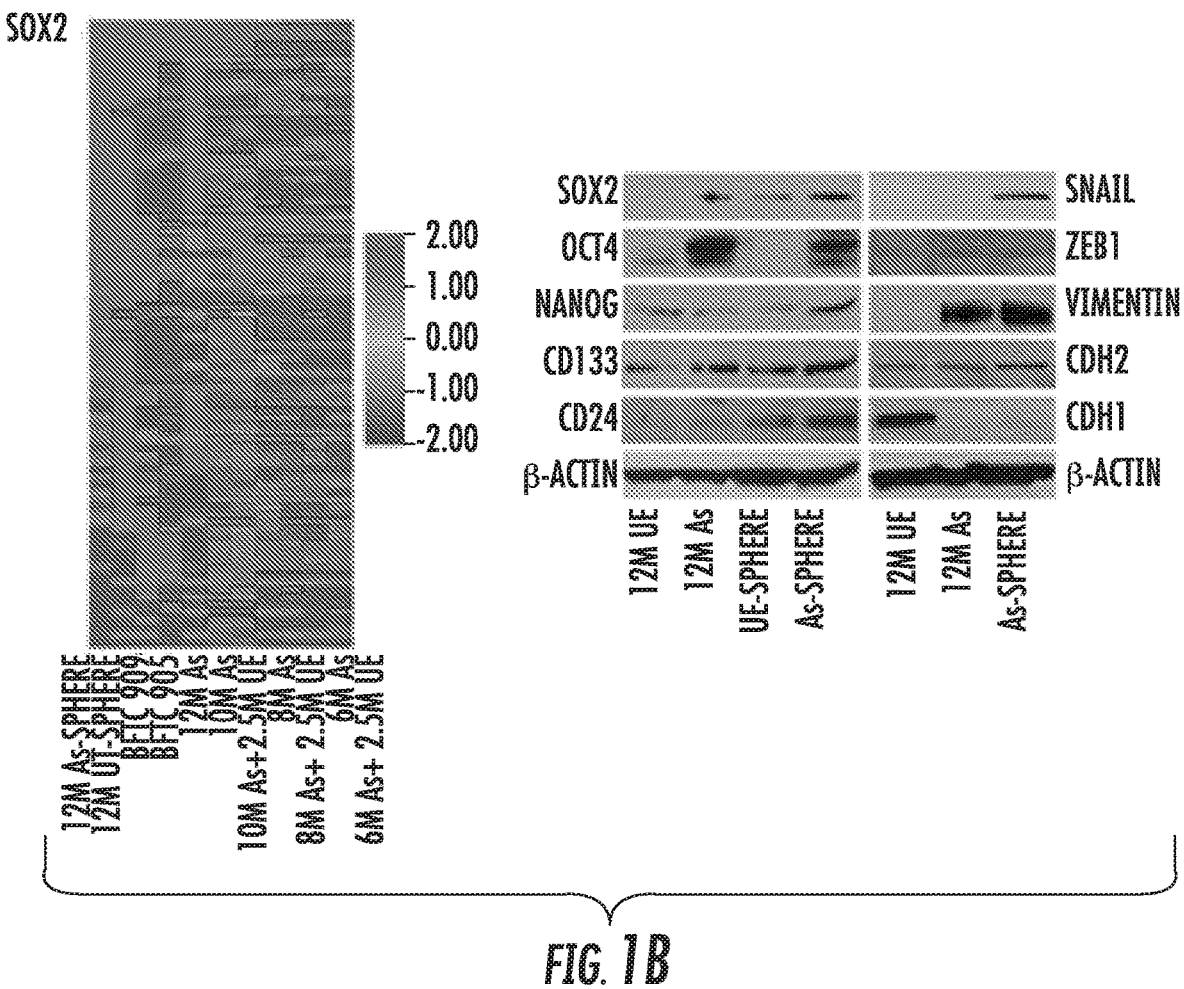
Figure 1C:
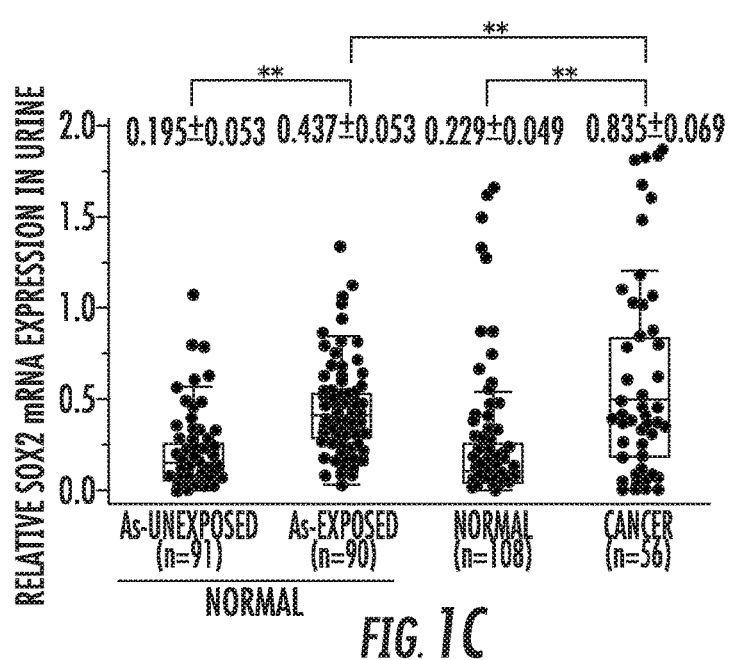

Chronic arsenic exposure irreversibly endowed normal urothelial cells with increased tolerance to arsenic toxicity and aggressive properties, including stemness properties (FIGS. 1A and S1). The inventors found that SOX2 was gradually and irreversibly overexpressed, in line with acquisition of spheroid-forming and self-renewal abilities in the stem cell-specific RT-PCR array (FIG. 1B and Table S1). In addition, several stem cell factors (OCT4 and NANOG), stem cell markers (CD133 and CD24), and mesenchymal markers (CDH2 and vimentin) were unregulated in arsenic exposed (As)-cells, and more so in As-spheroid cells (FIGS. 1B and S2A). Arsenic is present in cigarette smoke, and similar findings were observed in our in vitro smoking-induced stepwise model (FIG. S2B-D). In urine samples, SOX2 expression was significantly higher in As-subjects and cancer-subjects (FIG. 1C). Moreover, genetic knockdown of SOX2 suppressed the malignant stemness properties (FIG. S2E-G). Collectively, the inventor's findings indicate that chronic arsenic exposure drives SOX2 expression in association with malignant stem cell properties in addition to EMT.

Figure 1D:
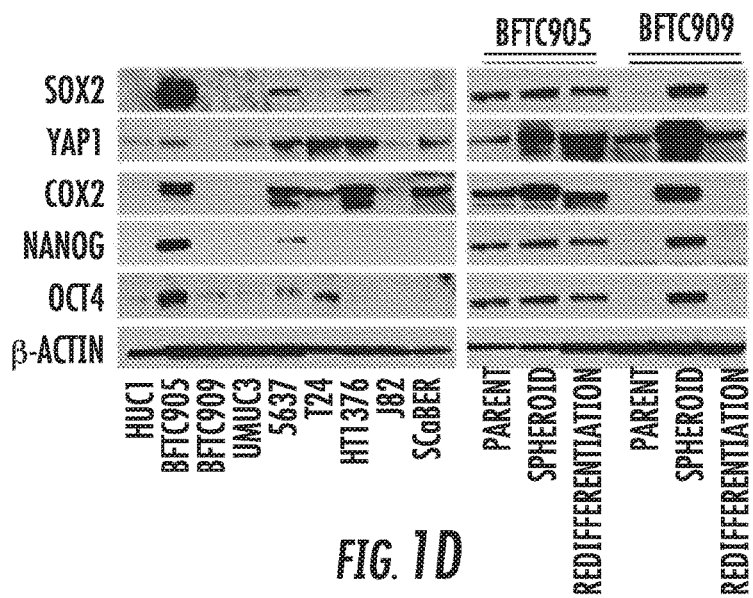
Figure 1E:
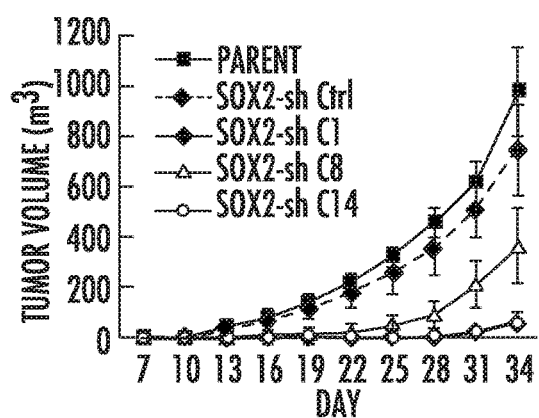
Figure 1F:
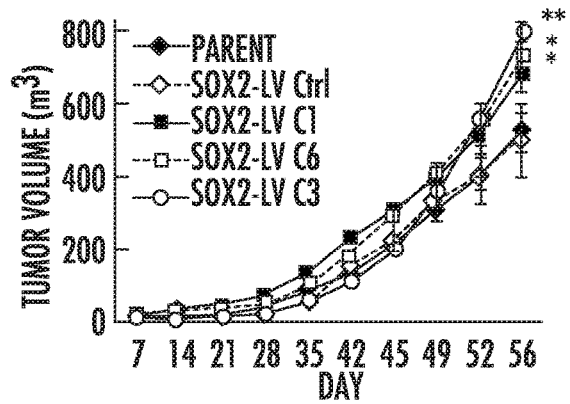

The results in the arsenic stepwise model prompted the inventors to investigate the role of SOX2 as an oncogene. SOX2 was preferentially expressed in bladder cancer cell lines compared with normal urothelial HUC1 cells, and a higher expression level of SOX2 was observed in spheroid cells compared with parental or redifferentiated cells (FIGS. 1D and S3A-B). The inventors found that SOX2 was a prominent factor for CSC properties using stable SOX2 knockdown (SOX2-sh) and overexpressed (SOX2-LV) cells (FIGS. 1E-F and S3C-G). Moreover, SOX2-sh spheroid cells showed significantly reduced tumor initiation in limiting dilution xenografts, a defining feature of CSCs, while SOX2-LV cells exhibited aggressive effect (FIGS. 1E-F). Notably, SOX2 knockdown attenuated malignant stemness properties even in BFTC 909 cells that expressed SOX2 faintly (FIGS. 1D and S3C-H), indicating its crucial role in urothelial CSC maintenance. Finally, SOX2 governed the expression of various cellular stemness-related molecule consistently, including the regulation of OCT4, NANOG, CD24, and CD133 in parental and the spheroid cells (FIGS. S4A-C). In addition, we demonstrated a potential of $CD24^+/$ CD133+ as a surface marker to isolate SOX2-expressing CSCs (FIGS. S4D-F and SS).

Chronic Arsenic Exposure Induces a Specific Gene Signature

The inventors found that arsenic exposure enriched EGFR, YAP1, and PTGS2 (encoding COX2) signatures in expression profiling on As-cells (FIGS. 1G and S6A). Interestingly As-cells were sensitive to the EGFR inhibitor erlotinib, similar to basal-type bladder cancer cell lines, except for BFTC 905 cells harboring an NRAS mutation that drives erlotinib resistance as reported previously (3) (FIG. 1H). Moreover, enrichment of the basal-type gene signature was observed in As-cells as well as BFTC 905 cells using four different data sets of basal-type UCB including The Cancer Genome Atlas (TCGA) data (2-5) (FIGS. S6B-D and Table S2).

The COX2/PGE2-Let-7 Axis Regulates SOX2 Expression

Figure 2A:
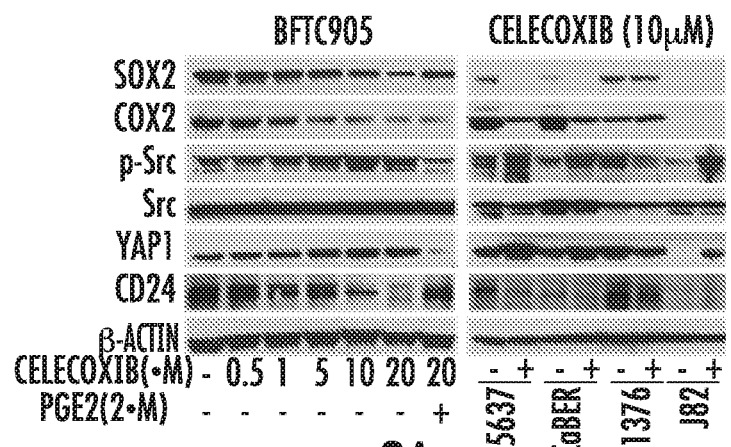
Figure 2B:
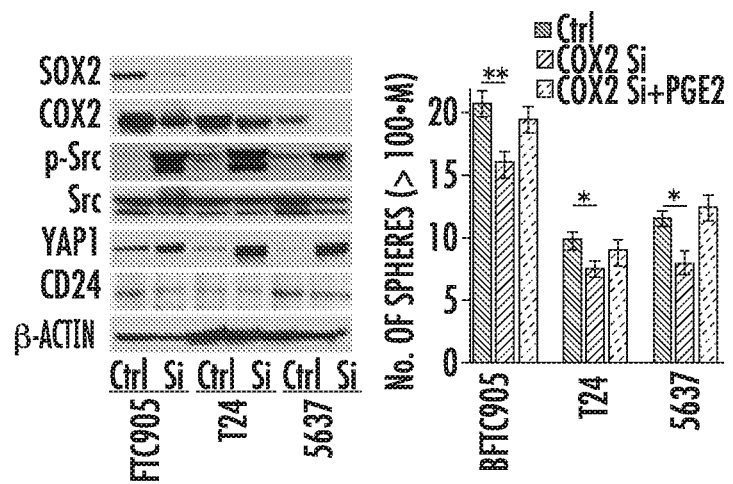
Figure 2C:
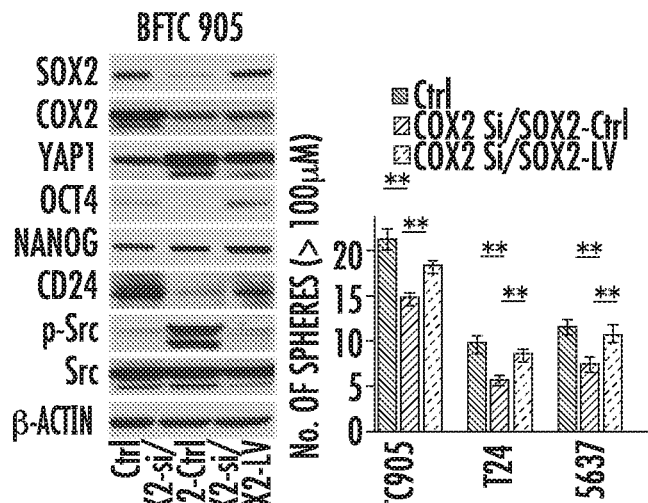

We found concomitant upregulation of SOX2, COX2 and YAP1 in arsenic-induced malignant stem cells (FIGS. 1B, 1G, S3B, and S6A), bladder cancer spheroid cells (FIGS. 1D and S3B), and CD24+/CD133+ cells (FIG. S5D). To test the link between COX2/PGE2 and SOX2 in urothelial CSCs, we pharmacologically and genetically inhibited COX2, which consistently led to SOX2 downregulation (FIGS. 2A-B and S7A). Moreover, PGE2 restored celecoxib (COX2 inhibitor)-repressed SOX2 expression and sphere-forming ability (FIGS. 2A-B and S7A-B). In addition, another COX2 inhibitor etodolac and the PGE2 receptors EP4-specific antagonist resulted in the dramatic reduction of SOX2 expression and sphere formation (FIG. S7C-D). Induction of SOX2 in COX2 knockdown cells rescued CSCs properties as determined by the sphere formation assay and expression of CSC-related molecules, supporting the role of the COX2/PGE2-SOX2 axis in maintaining urothelial CSCs (FIG. 2C).

Figure 2D:
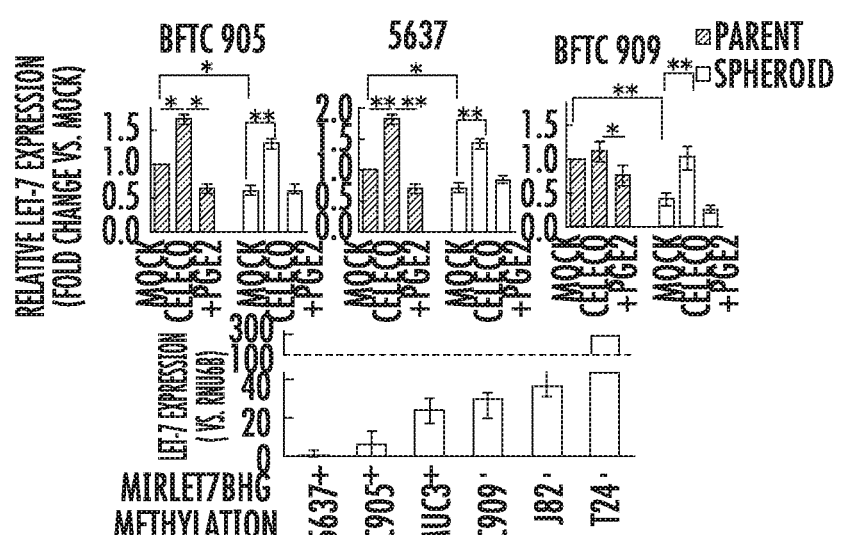
Figure 2E:
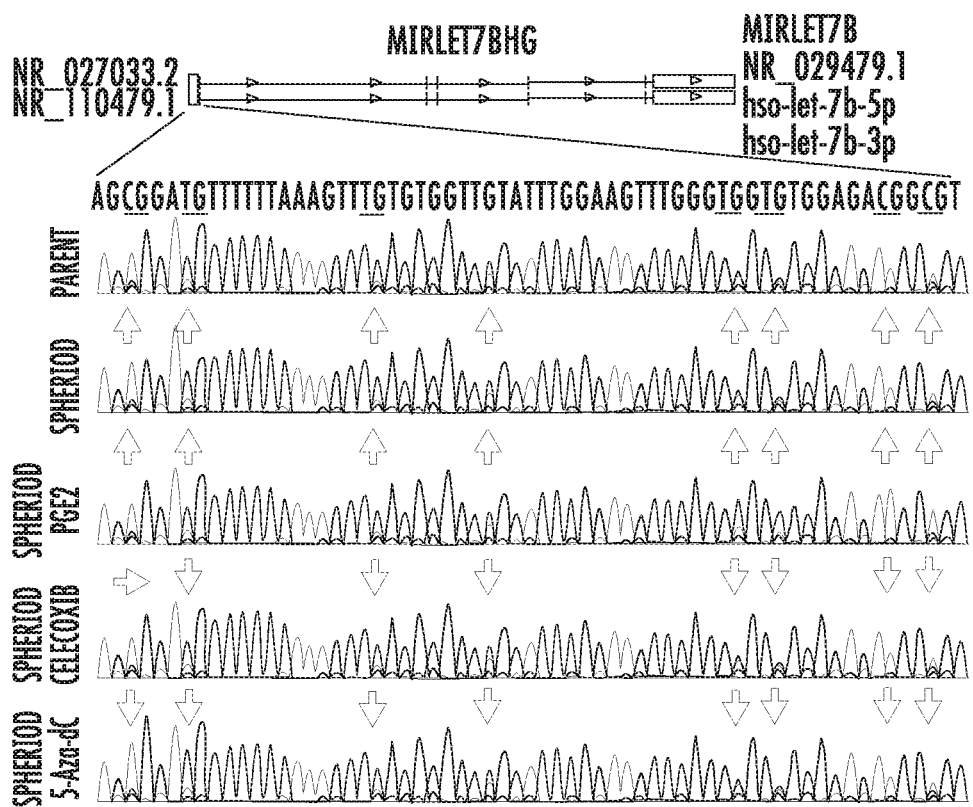

Recently, several microRNAs (miRNAs) have attracted attention in CSC maintenance. To understand the potential link between COX2/PGE2 signaling and miRNA-mediated regulation of SOX2, we tested the expression of a panel of miRNAs in BFTC 905 cells treated with or without the COX2 inhibitor or PGE2. COX2 inhibitor induced expression of several miRNAs, and addition of PGE2 reduced these expression (FIG. S7E). Since let-7 has been shown to regulate CSC functions as a tumor-suppressive miRNA, the inventors focused on the mechanistic role of this miRNA on urothelial CSC maintenance. Expression of let-7 was significantly downregulated in spheroid cells compared with parental cells, while inhibition of COX2 consistently induced its expression, and PGE2 reduced its expression (FIG. 2D). As promoter methylation of the let-7 host gene is one of the regulatory mechanism for let-7 expression, the inventors assessed whether COX2/PGE2 induced promoter methylation and silencing of let-7 during spheroid formation. Promoter methylation of the let-7 host gene was observed in spheroid and PGE2-treated cells that showed a trend toward lower let-7 expression (FIG. 2D-E). Treatment with the COX2 inhibitor or the demethylating agent 5-aza-2'-deoxycytidine (5-Aza-dC) demethylated the promoter regions and led to restoration of let-7 expression (FIGS. 2D-F and S7F). In addition, COX2/PGE2 induced DNA methyltransferase (DNMT) 1 and 3A (FIG. 2G). Thus, COX2/PGE2 induced promoter methylation of let-7 host genes and silencing of let-7 via DNMT 1 and 3A during spheroid formation. Moreover, we observed a marked reduction of the high-mobility group AT-hook 2 (HMGA2) and SOX2 expression via let-7 induction (FIG. 2H). Additionally, rescue of let-7-attenuated sphere-forming ability by induction of SOX2 suggests that the COX2/PGE2-let7-HMGA2-SOX2 axis directly related to urothelial CSC traits (FIG. 2I).

YAP1 and COX2/PGE2 Signaling Pathways Mutually Compensate Through Negative Feedback of SOX2 to Maintain Urothelial CSCs YAP1 regulated SOX2 expression, sphere-forming ability, and tumorigenicity (FIGS. 3A-D and S8A-C). Furthermore, induction of SOX2 rescued YAP1 knockdown-attenuated expression of CSC factors and self-renewal ability, while knockdown of SOX2 attenuated these effects and tumorigenicity (FIG. 3E-G), suggesting that YAP1 contributes to urothelial CSC traits via SOX2.

Figure 3A:
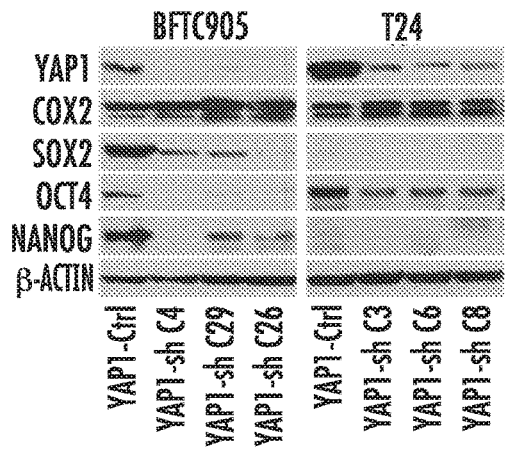
Figure 3B:
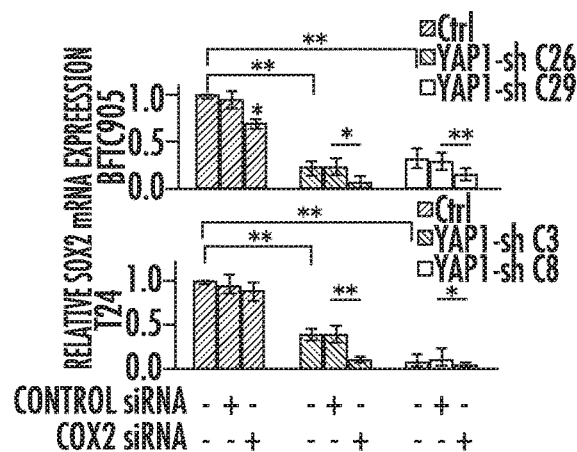
Figure 3C:
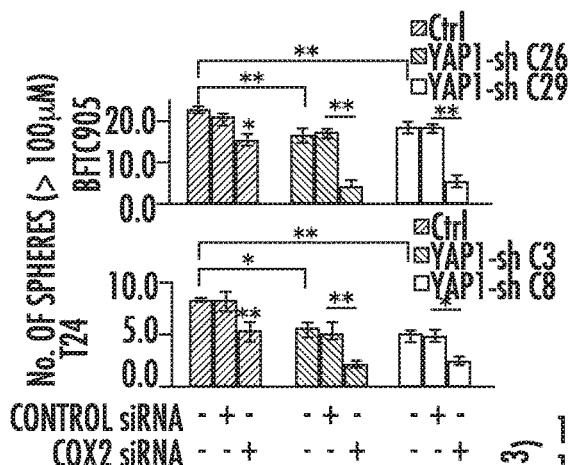
Figure 3D:
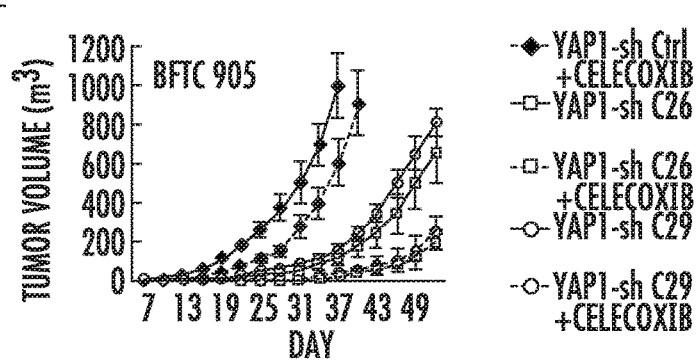
Figure 3D:
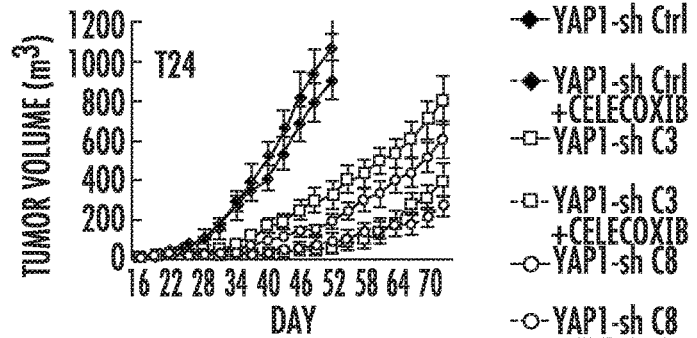
Figure 3E:
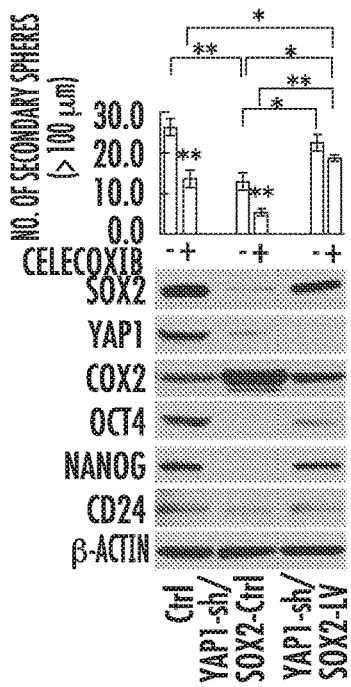
Figure 3F:
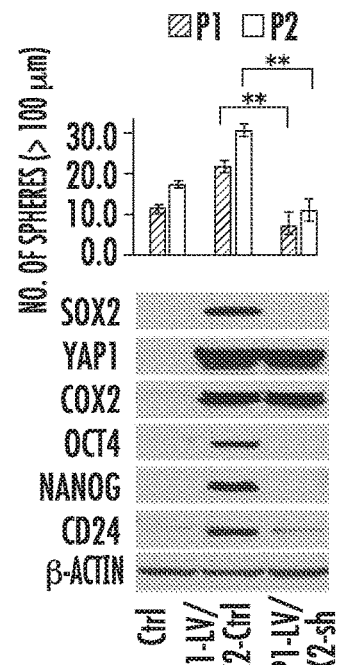
Figure 3G:
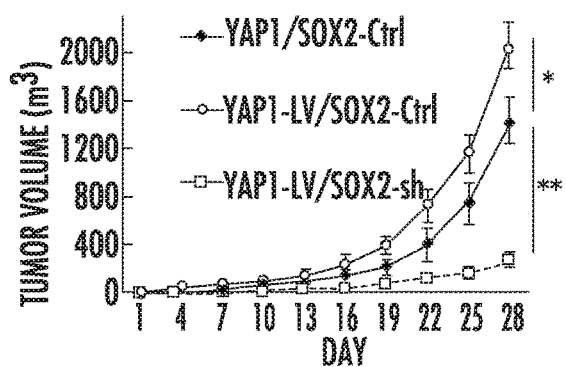
Figure 3H:
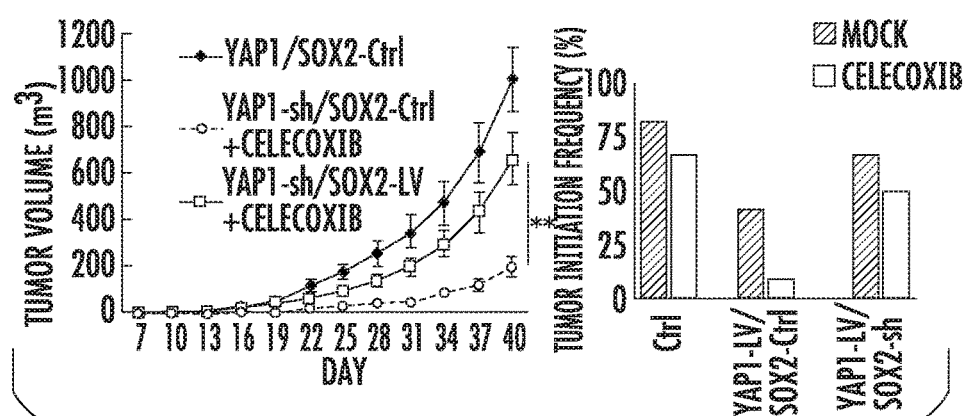

Since COX2 has been reported as a target gene of YAP1 (21), we assessed whether YAP1 activates COX2/PGE2 signaling in UCB. Both forced overexpression and knockdown of YAP1 led to COX2 induction (FIGS. 3A and S8A). Of note, COX2 overexpression due to YAP1 knockdown could not increase SOX2 expression and stemness properties (FIG. 3A-D), suggesting the presence of a predominant YAP1-SOX2 axis independent of COX2 signaling, presumably via direct binding with the SOX2 promoter (22). Conversely, inhibition of the COX2/PGE2-let-7 signaling axis induced YAP1 overexpression (FIGS. 2A-C, 2I, S7A, and S7C), and dual inhibition of YAP1 and COX2 resulted in a significant reduction of SOX2 expression, CSC traits, and tumorigenicity compared with inhibition of either alone (FIG. 3B-D). Again, induction of SOX2 rescued in vivo tumorigenicity and tumor initiation attenuated by the dual inhibition of YAP1 and COX2 (FIG. 3H). These findings indicate that YAP1 and COX2/PGE2 signaling pathways mutually compensate to maintain SOX2 expression, CSC traits, and tumorigenicity. Moreover, we determined that the compensation occurs through negative feedback of SOX2 by demonstrating downregulation of both COX2 and YAP1 via SOX2 induction (FIGS. 2C, 2I, 3E, and S4B) and upregulation via SOX2 knockdown (FIG. S4B). Since apoptotic tumor cells release COX2-derived PGE2 (13), abolishment of anti-apoptosis protected by the YAP1-SOX2 axis is likely responsible for the production of COX2/PGE2 due to YAP inhibition (FIG. S8D-G). Moreover, in line with implication of Src in regulating YAP1, we found activation of Src along with YAP1 overexpression by inhibition of the COX2/PGE2-let-7-SOX2 signaling axis (FIGS. 2A-C, 2I, S4B, S7A, and S7C), and COX2 inhibitor-induced YAP1 was downregulated by treatment with the Src inhibitor (FIG. S8H), indicating Src-dependent YAP1 overexpression through negative feedback of SOX2.

In human primary tumor samples, tumors showed trends toward higher SOX2, COX2, and YAP1 and lower let-7 expression compared with matched normal epithelium, and the liner correlation was observed (FIGS. 4A-B and S9A). Moreover, the combination of YAP1 and COX2 provided more rigorous prognostic stratification than either alone or SOX2 (FIG. S9B).

COX2, YAP1, and SOX2 Expression are Correlated with Immunosuppression

The inventors found YAP1-dependent production of TNFα, IL-6, and TGF-β and YAP1-SOX2 axis-dependent production of IL-4 and IL-10 (FIG. 5A). TGF-β, IL-6, and IL-10 are responsible for expansion of regulatory T-cells (Tregs) in tumor-bearing hosts (24), which uniquely expressed FOXP3. The number of FOXP3-positive tumor infiltrating lymphocytes (TILs), but not CD8-positive TILs, was increased within tumor regions with YAP1, COX2, or SOX2 expression (FIG. 5B and S9C). It was reported previously that myeloid-derived suppressor cells (MDSCs)

maintain a state of immunologic anergy and tolerance, and both YAP1 and COX2/PGE2 promote homing of MDSCs into tumor (26, 27). To assess the relevance of YAP1 and COX2 to MDSCs recruitment in UCB, we analyzed TCGA UCB gene expression data using the MDSC-related gene signature. Both YAP1 and COX2 were expressed at higher levels in the MDSC-high group compared with MDSC-low group (FIG. 5C).

YAP1 and COX2 Inhibitors Attenuates SOX2 Expression and Tumor Growth

Figure 6A:
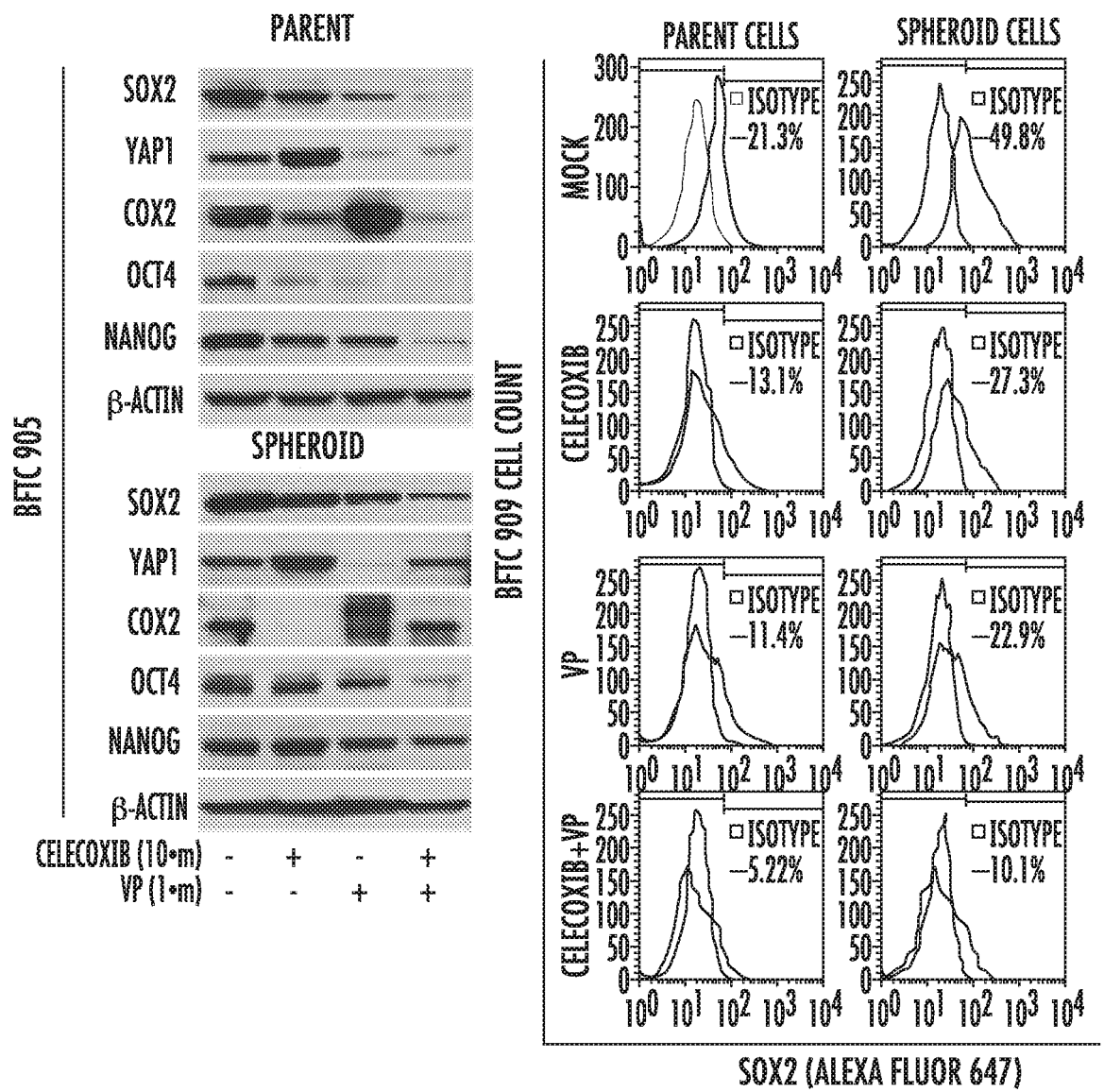
Figure 6B:
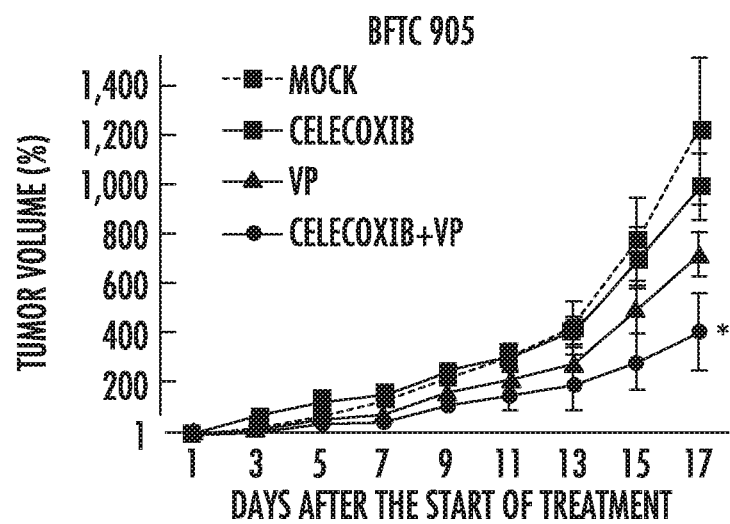
Figure 6C:
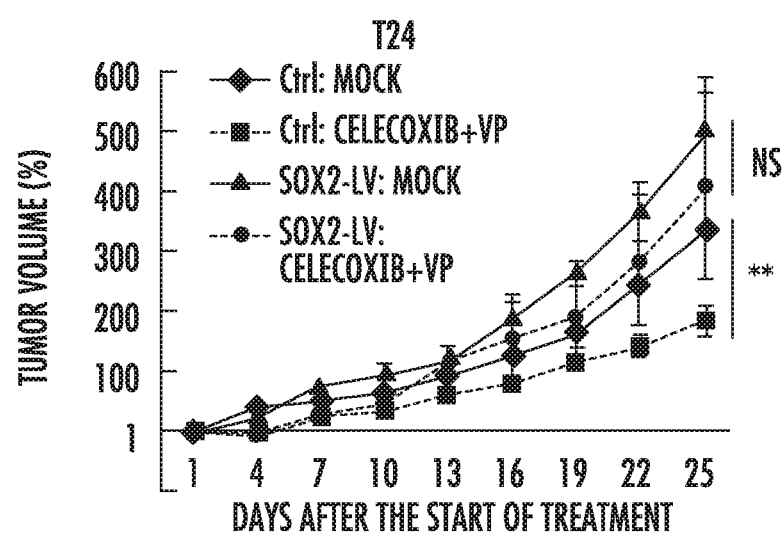

The inventors assessed the therapeutic efficacy of dual inhibition of COX2 and YAP1 using the pharmacological inhibitor celecoxib and verteporfin (VP). Consistent with results of YAP1 genetic knockdown, VP reduced expression of SOX2 and its related molecules, and induced COX2 expression in a dose-dependent manner (FIGS. 6A and S10A). Dual inhibition of COX2 and YAP1 drastically reduced stem cell properties along with SOX2 expression compared with either inhibitor alone, potentially by disrupting the compensatory mechanism (FIGS. 6A-B and S10B). Moreover, the therapeutic efficacy of dual inhibition was attenuated by SOX2 induction (FIG. 6C), strengthening the rationale for dual inhibition of COX2/PGE2 and the YAP1 signaling axis to fully block SOX2 expression and its negative feedback mechanism.

Figure 6D:
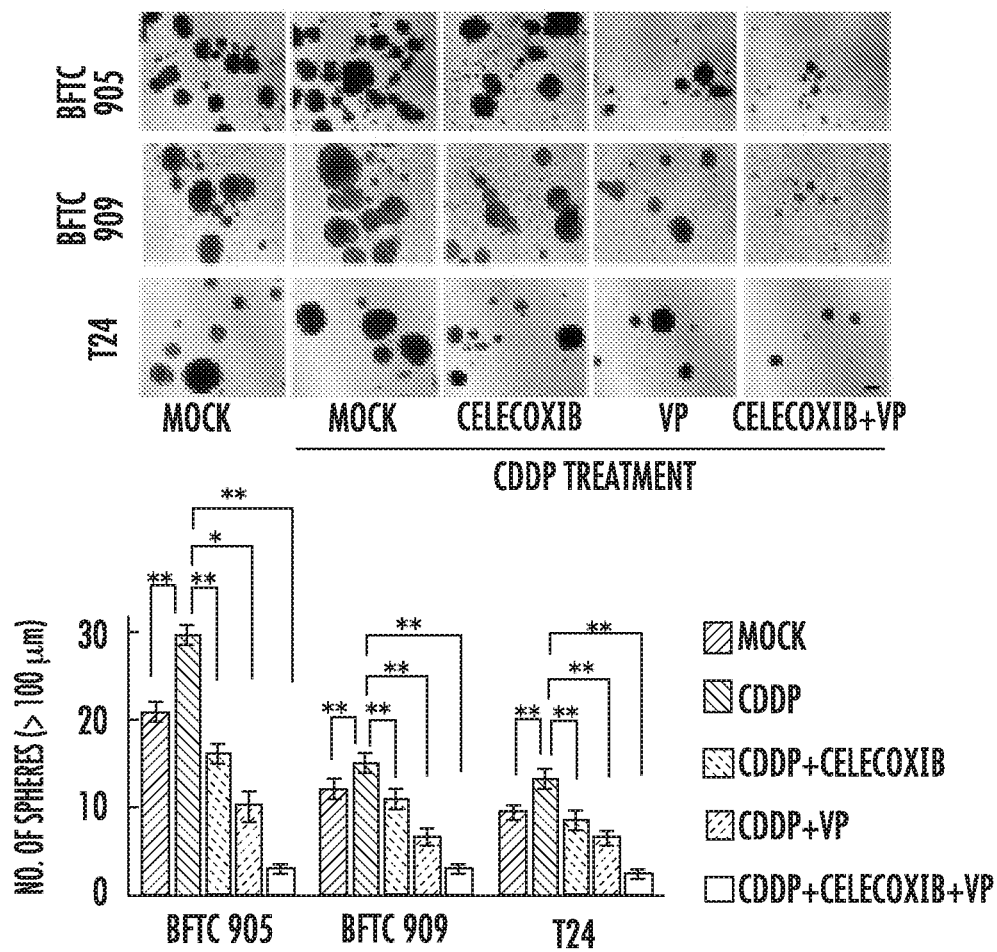
Figure 6E:
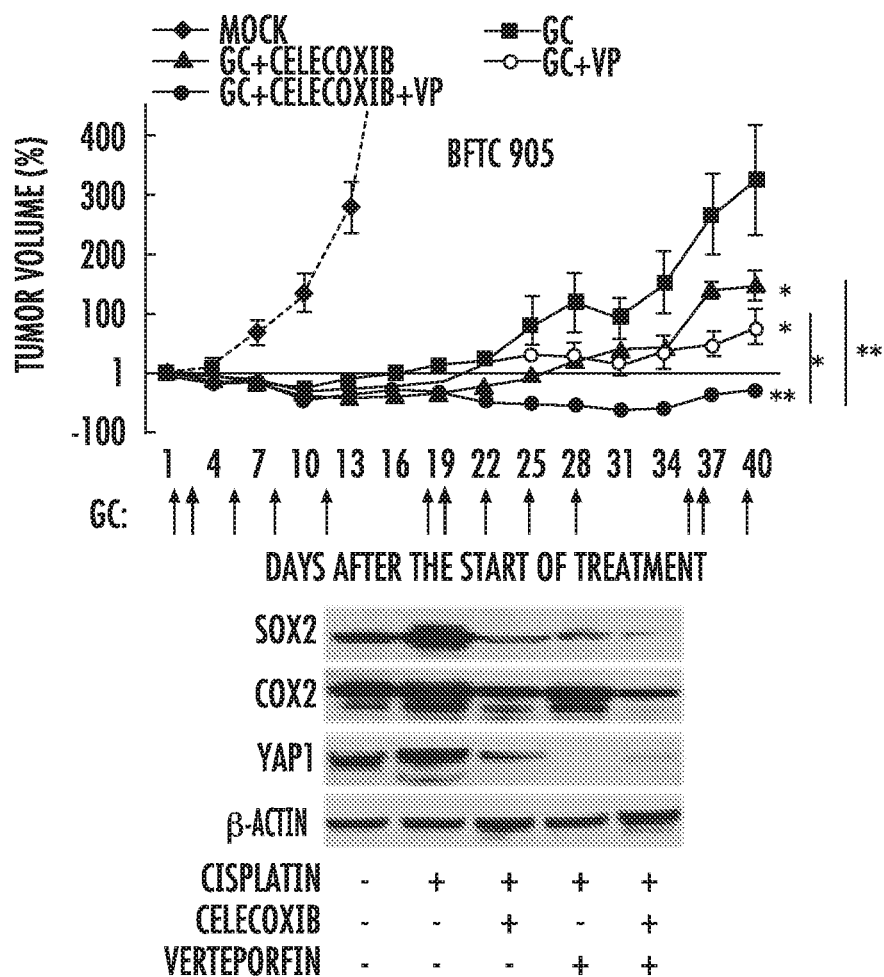
Figure 6F:
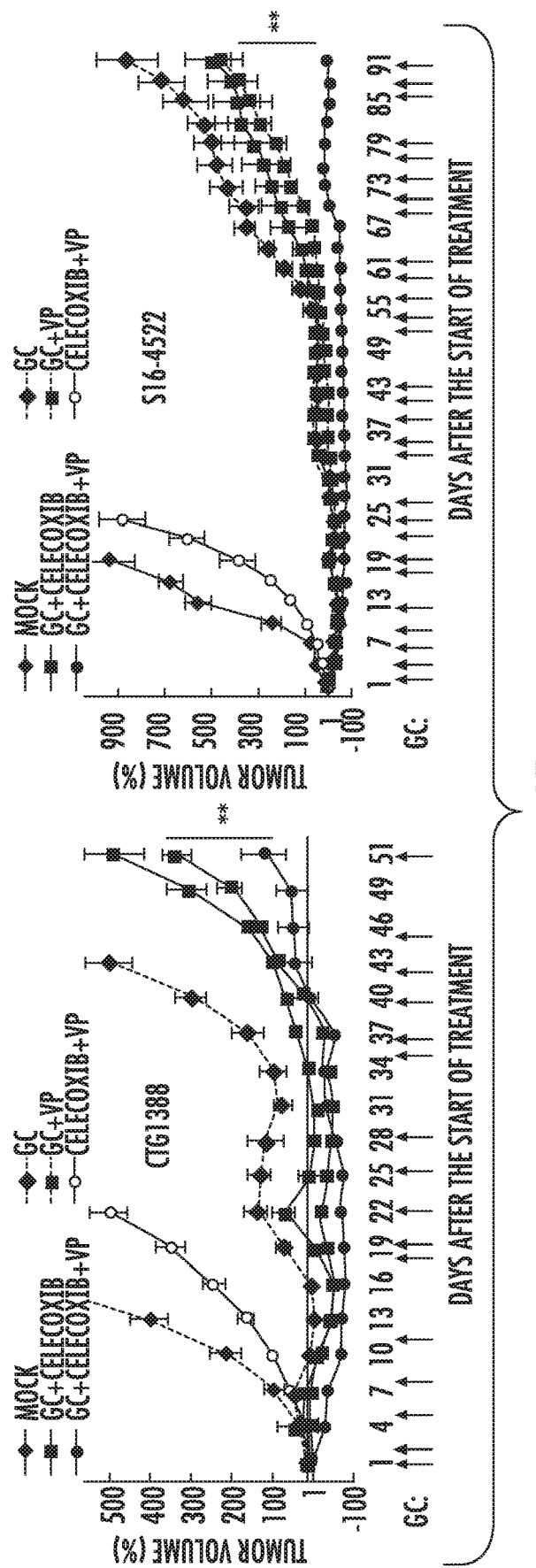

YAP1 and COX2 Inhibitors Enhance Chemotherapy Efficacy in Patient-Derived Xenograft (PDX) Models The inventors found that cisplatin (CDDP) chemotherapy resulted in increased sphere formation and overexpression of YAP1, SOX2, and COX2 (FIGS. 6D and S10C-D). Chemotherapy-induced COX2 and YAP1 signaling may promote CSC expansion via SOX2 overexpression and subsequent chemotherapy resistance. Indeed, dual inhibition of COX2 and YAP1 remarkably repressed CSC expansion; and SOX2, COX2 and YAP1 expression following CDDP treatment (FIGS. 6D and S10D-E). Moreover, gemcitabine (GEM) plus CDDP (GC) chemotherapy, the standard regimen for UCB, combined with dual inhibitors demonstrated significantly continuous tumor regression and reduced SOX2 expression in the more heterogenous and clinically relevant PDX models as well as cell-derived xenograft models (FIGS. 6E-F and S10E-G). In addition, replacing celecoxib with an EP4 antagonist showed similar efficacy (FIG. S10F).

Figure 7A:
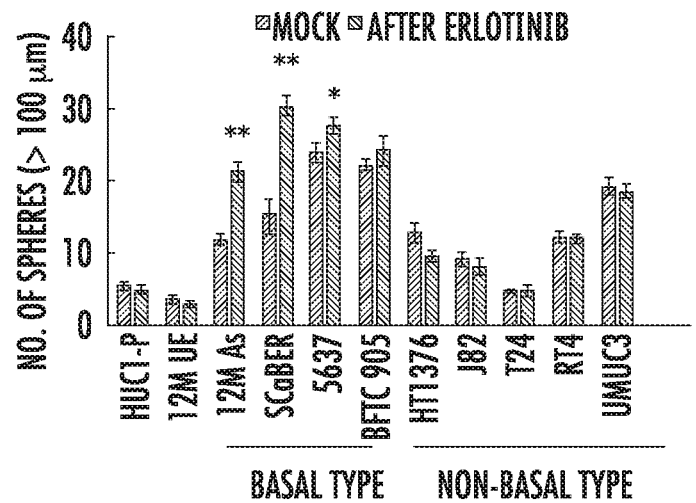
Figure 7B:
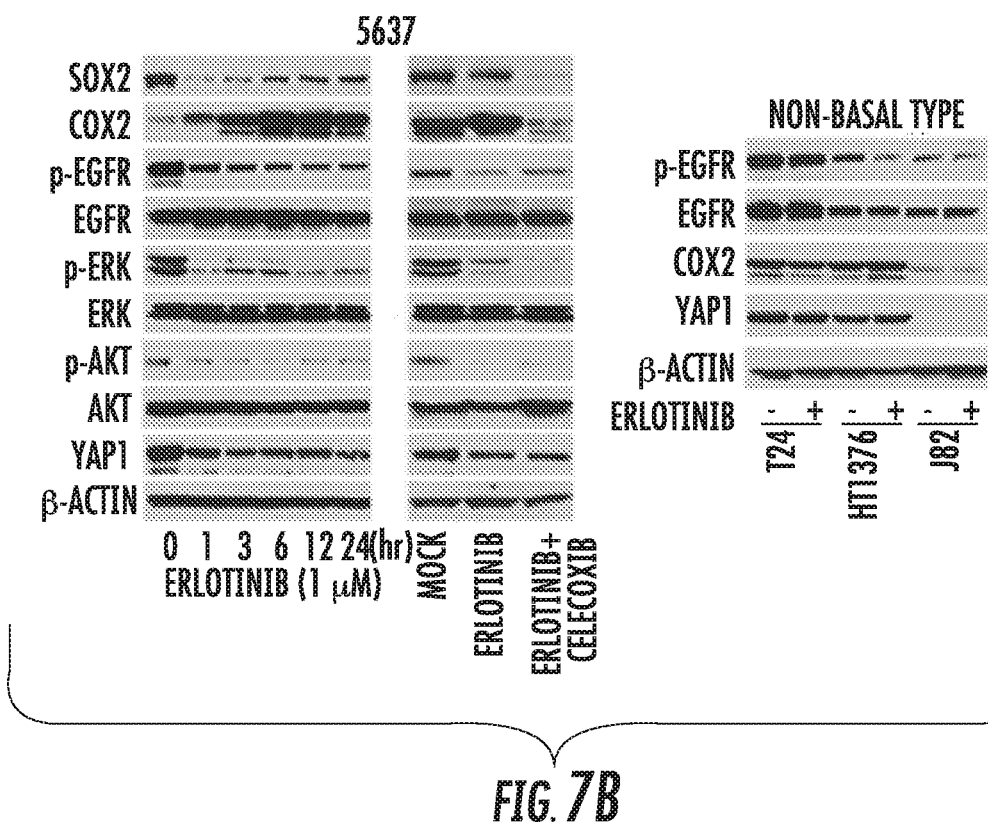
Figure 7F:
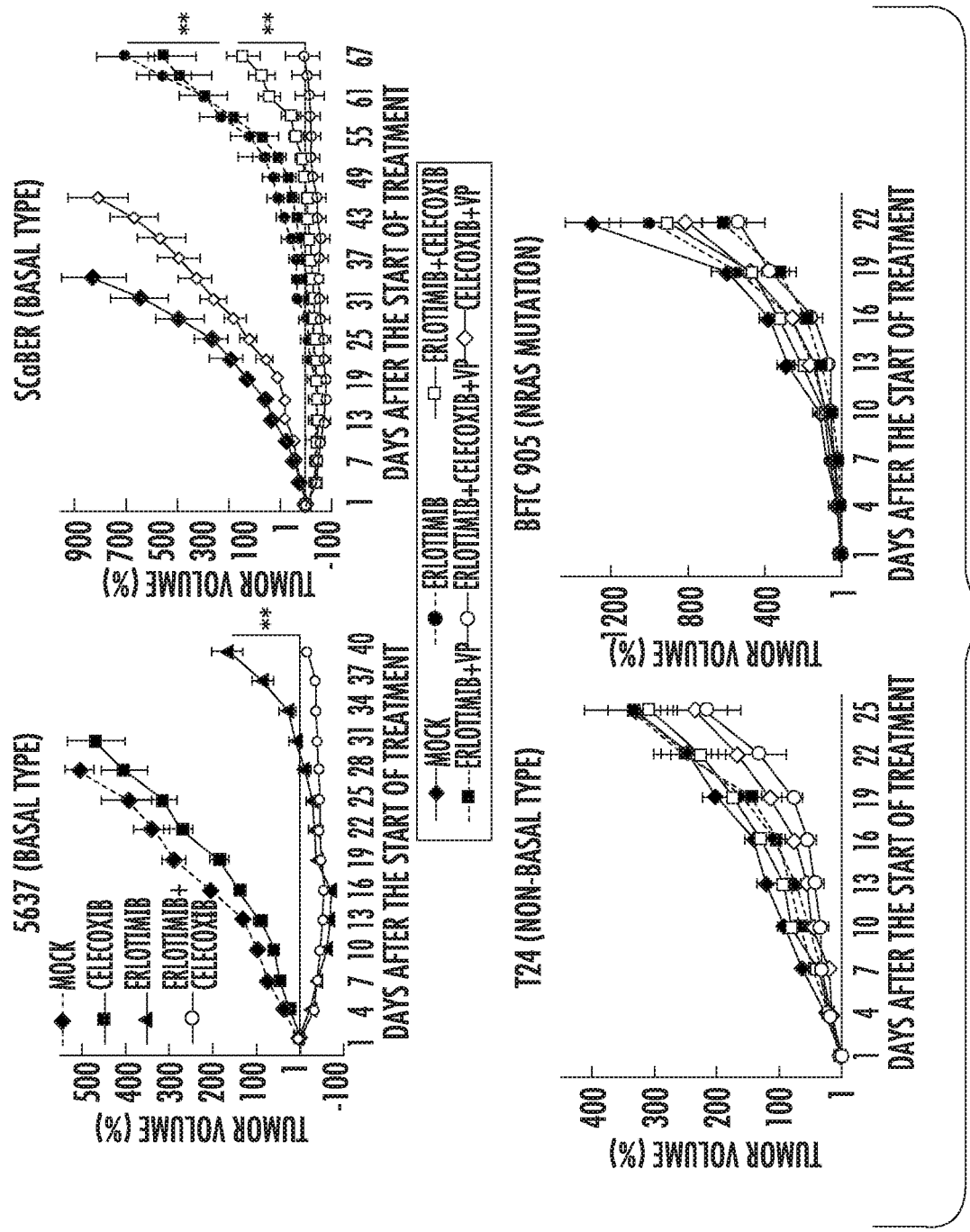

Triple Blockade of EGER, COX2, and YAP1 Results in Continuous Tumor Response in Basal-Type Bladder Cancer Although the inventors confirmed the efficacy for EGFR-targeted therapy in basal-type cells (FIG. 1H), the treatment also resulted in an enriched number of spheres (FIG. 7A). Intriguingly, the level of SOX2 expression was decreased at 1 hour after treatment with erlotinib and then gradually increased in proportion to increased COX2 expression, and addition of the COX2 inhibitor impaired the increased SOX2 expression and sphere formation in a basal-type specific context (FIGS. 7B-C and S7A), suggesting that the COX2-SOX2 axis plays a role in CSC enrichment following erlotinib treatment. In contrast, treatment with erlotinib resulted in continuously decreased YAP1 expression along with suppressed activation of AKT and extracellular signal-related kinase (ERK), and EGF-stimulated EGFR signaling led to increased YAP1 and SOX2 expression (FIGS. 7B and D). Moreover, inhibition of PI3K/AKT reduced YAP1 and SOX2 expression in basal-type but not non-basal type cells, whereas inhibition of ERK did not affect the expression of these molecules (FIG. 7E). Of note, addition of the COX2 inhibitor was no longer able to induce YAP1 expression because of the inhibition of the EGFR-PI3K/AKT-YAP1 signaling pathway by erlotinib treatment (FIG. 7B). Therefore, combined inhibition of EGFR and COX2 may be more effective in repressing CSC expansion via SOX2 than the EGFR inhibitor alone, as supported by its therapeutic efficacy in the basal-type xenograft models (FIG. 7F).

Figure 7G:
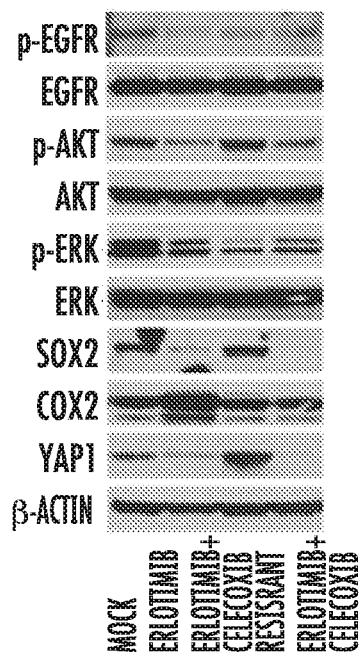
Figure 7H:
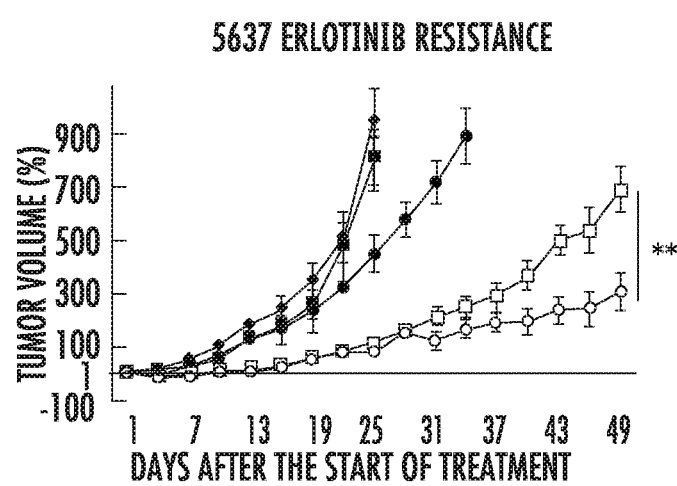

Intriguingly, tumors with acquired resistance to EGFR inhibitor exhibited re-activated PI3K/AKT signaling and concomitantly elevated YAP1 and SOX2 levels, whereas EGFR-MAPK signaling remained suppressed by treatment with erlotinib (FIG. 7G). YAP1-SOX2 axis via re-activated PI3K/AKT signaling may be also relevant to acquired resistance to the EGFR inhibitor, as demonstrated by our findings that the resistant tumors again became sensitive to EGFR inhibitor in combination with YAP1 inhibitor, and further addition of COX2 inhibitor resulted in significantly continuous efficacy by suppressing of the compensatory mechanism (FIG. 7H). Finally, we found that concurrent inhibition of EGFR, COX2, and YAP1 as the initial treatment led to long-term therapeutic efficacy by preventing emergence of the acquired resistance pathway (FIG. 7F).

A growing body of evidence supports that rare CSCs are at the top of a cellular hierarchy within neoplasms, resulting in tumorigenesis, metastasis, and treatment failure. Therefore, identification of mechanisms behind the properties of urothelial CSCs might pave the way for novel therapeutic strategies to improve prognosis in UCB. Here, the inventors provide a rationale for targeting COX2/PGE2 and YAP1 signaling pathways to attenuate CSCs by uncovering how COX2/PGE2 induces CSC expansion and interacts with YAP1 to maintain urothelial CSCs (FIG. 8).

SOX2 has been implicated in malignant stemness properties in several types of cancer, while it acts as a tumor suppressor in gastric cancer, indicating a context dependent behavior of SOX2. In the present invention, the inventors found that SOX2 acts as a critical oncogene linked with malignant stemness properties in UCB and regulates OCT4 and NANOG, which are also essential transcription factors not only to regulate early development and iPSCs but also to maintain CSCs. Moreover, SOX2 also regulates the drug efflux transporter ATP-binding cassette subfamily G member 2 (ABCG2) (FIGS. S4A and S5D), which provides CSCs with a selective survival advantage in response to chemotherapy. Thus, our functional and molecular analyses suggest that SOX2 may be a master regulator that governs many properties of urothelial CSCs.

The COX2/PGE2 pathway plays a key role in tumor-promoting inflammation, and the inhibition of this pathway suppresses CSCs. We revealed that COX2/PGE2 signaling induces promoter methylation of the let-7 host gene via upregulation of DNMT 1 and 3A expression, resulting in downregulated let-7 expression and subsequent SOX2 expression. Since let-7 negatively regulates HMGA2, which induces SOX2 expression through direct binding to the SOX2 promoter, our findings point to an important role of the COX2/PGE2-let-7-HMGA2-SOX2 axis in urothelial CSCs generation and maintenance. COX2/PGE2 signaling also affected expression of miR-21, miR-126, miR-296, and miR-200c (FIG. S7E-F), which has been implicated as a tumor suppressor in SOX2 regulation. The promoters of these miRNAs, except for miR-21, are also densely methylated in spheroid cells and demethylated by treatment with celecoxib. Collectively, COX2/PGE2-induced epigenetic silencing of tumor-suppressor miRNAs that lead to SOX2 induction may be one of the crucial mechanisms of CSC expansion. Therefore, it is relevant to target this pathway to eradicate CSC and to eliminate the root of the tumor-promoting inflammatory environment.

The Hippo signaling pathway is an evolutionarily conserved cascade that controls organ size by regulating cell proliferation, differentiation, apoptosis, and stem cell biology via negative regulation of the main downstream mediator YAP1 activity. However, its contribution to urothelial CSCs and relationships with SOX2 and COX2/PGE2 in UCB remain elusive. The present invention revealed that YAP1 and COX2/PGE2 signaling are activated to cooperatively induce SOX2 expression under steady-state conditions in urothelial CSCs and are mutually compensated to maintain urothelial CSCs via a negative feedback mechanism of SOX2, possibly explaining why the COX2 inhibitor alone was insufficient for preventing recurrence in clinical studies.

SOX2 may be an undruggable target because of its lack of small molecule binding pockets. In addition, induction of SOX2 could not completely recover the malignant stem cell properties attenuated by inhibition of COX2 and YAP1 (FIGS. 3E and 3H), raising the possibility that YAP1 and COX2/PGE2 signaling also contribute to maintaining SOX2-independent CSCs. Moreover, the combination of YAP1 and COX2, but not SOX2, provides precise prognostic stratification. SOX2-expressing cells are functionally heterogeneous, among which a CD133$^+$/CD24$^+$ subpopulation results in poor outcome and confers urothelial CSC attributes and higher expression of YAP1 and COX2 (FIGS. S5 and S9B). Therefore, targeting both YAP1 and COX2/PGE2 signaling pathways is likely indispensable for full eradication of urothelial CSCs, and GC chemotherapy combined with COX2 and YAP1 inhibitors was sufficient for tumor shrinkage by targeting both CSCs and the bulk of cancer cells. Of note, celecoxib and VP have been approved for acute pain and macular degeneration, respectively, by the U.S. Food and Drug Administration, implying that these drugs are relatively safe. Indeed, we did not observe body weight loss of mice treated with these inhibitors compared with control. However, long-term use of selective COX2 inhibitors has raised concerns about an increased risk of serious cardiovascular events, and we demonstrated that PGE2 receptor EP4 may be an alternative pharmacological target to a COX2 inhibitor.

The poor results of EGFR-targeted therapy in clinical trials suggest that treatment success depends on selecting appropriate patients, and basal-type UCB may display higher benefit to EGFR-targeted therapy because of its dependence on this signaling pathway. However, the inevitable development of drug resistance presents a critical challenge for targeted cancer therapies. Rapid signaling feedback loops that modulate the cellular response to growth factor inhibition have been demonstrated as one resistance mechanism. COX2 is triggered rapidly, presumably through apoptosis due to the EGFR inhibitor and/or by a compensatory mechanism for inhibition of the YAP1-SOX2 axis. This effect may in turn protect CSCs from the treatment due to restoration of SOX2 expression and subsequent CSC enrichment. As another resistance mechanism, we revealed that activation of the YAP1-SOX2 axis via PI3K/AKT signaling re-activated another oncogenic bypass. Collectively, our findings suggest that COX2 and YAP1 signaling determine acquired resistance to treatment with the EGFR inhibitor via SOX2, and triple blockade of EGFR, COX2, and YAP1 may be an attractive therapeutic option to prolong efficacy for patients with basal-type UCB.

The escape of cancer cells from host immune surveillance has been considered as a prerequisite for tumor progression, and adaptive immunity has been shown to enrich CSCs. Tumor-infiltrating Tregs and MDSCs are key players in the tumor immune escape mechanism, and we found the link of YAP1 and COX2/PGE2 expression with the increased Treg infiltration and MDSC-related gene signature. Thus, dual blockade of YAP1 and COX2 may be also effective to enhance sensitivity to immunotherapy such as checkpoint blocking antibodies. Further studies are required to determine whether these pathways are viable therapeutic targets for overcoming immune evasion in UCB.

In summary, the present invention demonstrates that COX2/PGE2 and YAP1 signaling pathways mutually compensate to regulate urothelial CSCs via SOX2 and that activation of these pathways hampers the efficacy of systemic therapy by expanding CSC. The inventor's findings provide rationale to concurrently target these pathways with systemic therapy as an effective therapeutic strategy for UCB.

Embodiments of the disclosure concern methods and/or compositions for treating and/or preventing cancer in which modulation of the COX 2 and YAP 1 pathways are directly or indirectly related. In certain embodiments, individuals with a cancer such as bladder cancer or urothelial carcinoma, for example, are treated with a modulator of these pathway, and in specific embodiments an individual with cancer is provided a modulator of COX 2 and YAP 1, such as one or more inhibitors of COX 2 and YAP 1.

In certain embodiments, the level to which an inhibitor decreases COX 2 and YAP 1 activity may be any level so long as it provides amelioration of at least one symptom of a cancer, including bladder cancer and urothelial carcinoma. The level of enzymatic activity may decrease by at least 2, 3, 4, 5, 10, 25, 50, 100, 1000, or more fold compared to the level of activity in a standard or reference, in at least some cases.

An individual known to have cancer, suspected of having cancer, or at risk for having cancer may be provided an effective amount of one or more inhibitors of COX 2 and YAP 1, including celecoxib and verteporfin, for example. Those at risk for cancer may be those individuals having one or more genetic factors, may be of advancing age, and/or may have a family history, for example.

In particular embodiments of the disclosure, an individual is given an agent for cancer therapy in addition to the one or more inhibitors of COX 2 and YAP 1. Such additional therapy may include other chemotherapy treatments, for example. When combination therapy is employed with one or more inhibitor of COX 2 and YAP 1, the additional therapy may be given prior to, at the same time as, and/or subsequent to the one or more inhibitor of COX 2 and YAP 1.

Pharmaceutical Preparations

Pharmaceutical compositions of the present invention comprise an effective amount of one or more inhibitors of COX 2 and YAP 1 such as celecoxib and verteporfin, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one or more inhibitors of COX 2 and YAP 1 or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The one or more inhibitors of COX 2 and YAP 1 may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The inducer one or more inhibitors of COX 2 and YAP 1 may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semisolid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include one or more inhibitors of COX 2 and YAP 1, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the one or more inhibitors of COX 2 and YAP 1 may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the one or more inhibitors of COX 2 and YAP 1 are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, one or more inhibitors of COX 2 and YAP 1 may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,753,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound inhibitors of COX 2 and YAP 1 may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, one or more inhibitors of COX 2 and YAP 1 (for example, celecoxib and verteporfin) may be comprised in a kit.

The kits may comprise a suitably aliquoted of one or more inhibitors of COX 2 and YAP 1 and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the one or more inhibitors of COX 2 and YAP 1 and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The one or more inhibitors of COX 2 and YAP 1 composition(s) may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES/METHODS

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.
Compounds and Reagents Arsenic trioxide (AS2O3), Cisplatin (CDDP), Gemcitabine hydrochloride (GEM), COX2 selective inhibitor Celecoxib, YAP1 inhibitor Verteporfin (VP), demethylating agent 5-Aza-2'-deoxycytidine (5-Aza-dC), histone deacetylase inhibitor Trichostatin A (TSA) and Src tyrosine Kinase inhibitor PP2 were purchased from Sigma-Aldrich (St. Louis, USA). Prostaglandin E2 (PGE2) was purchased from Cayman Chemical (Ann Arbor, USA). EGFR small molecule inhibitor Erlotinib was purchased from BioVision (Milpitas, USA). The PI3K inhibitor LY294002 and MEK-1/2 inhibitor Trametinib (GSK1120212) were from Selleck Chemicals (Houston, USA). PGE2 receptor 4 (EP4) antagonist ONO-AE3-208, EP3 antagonist L-798,106, EP1 and EP2 antagonist AH 6809, and COX2 selective inhibitor Etodolac were purchased from Tocris Bioscience (Ellisville, USA). Recombinant human epidermal growth factor (EGF) and the fibroblast growth factors (FGF)-basic were purchased from PeproTech (New Jersey, USA).
Cell Lines and Tissue Samples Embryonic kidney cell line 293, SV-40 immortalized normal human urothelial cell line (HUC1), and bladder cancer cell lines 5637, HT-1376, J82, SCaBER, RT-4, T24, and UM-UC3 were obtained from American Type Culture Collection (ATCC; Manassas, Va., USA). Mediums were purchased from Mediatech (Manassas, USA) and supplemented with 10% FBS (Hyclone, Logan, USA) under a 5% $CO_2$ atmosphere at 95% relative humidity. HUC-1, T24, and 5637 cells were grown in F-12K, McCoy's 5A, and RPMI 1640 medium, respectively, and all other cells were grown Dulbecco's modified Eagle medium (DMEM). BFTC 905 and BFTC 909 cell lines were established from arsenic-exposed urothelial carcinoma subjects (9) and obtained from the German Collection of Microorganisms and Cell Cultures (Braunschweig, Germany). Re-authentification of cells was performed using PowerPlex 16 HS for short tandem repeats analysis at Genetic resource core facility, the Johns Hopkins University School of Medicine, Institute of Genetic Medicine, and all cell lines have been confirmed as authentic. To prepare in vitro arsenic model, we chronically exposed HUC1 cells to 1 µM arsenic trioxide, as described previously (10) and arsenic-exposed (As) cells and passage-matched arsenic un-exposed control (UE) cells were stock for each months until 12 months. To determine the arsenic withdrawal effect, we cultured cells exposed by arsenic for 10 months (10M As) and 12 months (12M As) without arsenic for 2.5 months (10M As+2.5M UE and 12M As+2.5M UE-cells).

Frozen human primary urothelial tumors and matched normal bladder tissue samples were kindly provided from Department of Pathology, The Johns Hopkins University School of Medicine. Ninety urine samples from subjects with high exposure to environmental arsenic and 91 samples from those with safe levels of arsenic were identified through the Health Effects of Arsenic Longitudinal Study (HEALS) cohort, an ongoing population-based prospective cohort study in Araihazar, Bangladesh (11). Arsenic levels in drinking water in Araihazar range from 0.1 µg/L to >100 µg/L. The cohort includes about 42,000 members, of whom 50% are exposed to arsenic >10 µg/L and 25% are exposed to >50 µg/L and approximately 10-12%>100 µg/L. Arsenic exposure status of subjects was determined through drinking water arsenic concentrations measured in the subject's primary tube-well used for water consumption. Arsenic concentrations in drinking water >10 µg/L were considered exposed (10). Fifty-six urine samples from subjects with UCB were kindly provided from Department of Pathology, The Johns Hopkins University School of Medicine. As a control, 108 urine samples were collected from the Johns Hopkins Urology patients with no history of genitourinary malignancy, and were evaluated by the cytopathology division of the department of pathology. Informed consent was obtained from the patients before sample collection. Approval for research on human subjects was obtained from the Johns Hopkins University institutional review boards. This study qualified for exemption under the U.S. Department of Health and Human Services policy for protection of human subjects [45 CFR 46.101(b)].
RNA Extraction and Quantitative Reverse Transcriptase Polymerase Chain Reaction (Q-RT-PCR)

Total RNA from cell lines was isolated using the RNeasy Plus Mini kit (Qiagen, Valencia, USA) according to the manufacturer's protocol. Total RNA extraction from bladder tissue was performed with the QIAzol Lysis Reagent (Qiagen) followed by phenol extraction and ethanol precipitation. Total RNA was eluted in DEPC treated water and stored at −80° C. Total RNA extraction from urine was performed using the MirVana miRNA Isolation Kit (Ambion, Austin, USA). These total RNA were converted to cDNA using the SuperScript III First-Strand Synthesis System (Life technologies, Carlsbad, USA), which was then used as a template for Q-RT-PCR. Q-RT-PCR was performed using the Fast SYBR Green Master Mix (Thermo Fisher Scientific, Waltham, USA) on a 7900HT Fast Real-Time PCR System (Life technologies) in triplicate. Primer sequences and the thermal cycling conditions were shown in the table below. Micro RNA (miRNA) extraction was performed using the MirVana miRNA Isolation Kit, and was reverse transcribed using TaqMan reverse transcription kit (Applied Biosystems, Foster City, USA) and miRNA-specific RT primers provided with TaqMan microRNA assays (Applied Biosystems). Q-RT-PCR for miRNAs was performed using the TaqMan Universal PCR Master Mix according to the manufacturer's protocol. SDS software (Applied Biosystems) was used to determine cycle threshold (Ct) values. Expression level was quantified relative to β-actin for mRNA and RNU6B for miRNA using the 2-ΔΔCt method (12).

Sequences of primers for Q-RT-PCR used in the present study

| Gene name | Forward primer (SEQ ID NOS 1-42, respectively, in order of appearance) | Reverse primer (SEQ ID NOS 43-84, respectively, in order of appearance) | Annealing temperatures |
|---|---|---|---|
| Q-RT-PCR[a] | | | |
| MT1A | AGAGTGCAAATGCACCTCCTGC | CGGACATCAGGCACAGCAGCT | 60 |
| MT2A | TCGCCATGGATCCCAACTG | AGGTTTGTGGAAGTCGCGT | 60 |
| HIF1A | CCCCAGATTCAGGATCAGACAGCC | TGGGACTATTAGGCTCAGGTGAAC | 58 |
| SOD1 | TGGGCCAAAGGATGAAGAGA | CACATCGGCCACACCATC | 58 |
| HMOX1 | TGGAAGACACCCTAATGTG | GGCCGTGTCAACAAGGATACTT | 58 |
| NFE2L2 | AACCAGTGGATCTGCCAACTACTC | CTGCGCCAAAAGCTGCAT | 58 |
| ABCC1 | GAGGAGGTGGAGGCTTTGATC | AAGTAGGGCCCAAAGGTCTTG | 58 |
| ABCC2 | GTGGCTGTTGAGCGAATAACTG | GCCTTTGCTGGGCCAAT | 58 |
| GSTP1 | AGAGCTGGAAGGAGGAGGTG | AGGTCTCCGTCCTGGAACTT | 58 |
| KRT6A | ACTTTCCACTGGCTCTCAAACTCT | ATACAGGCTTTGTACATCATAGGACTAGT | 58 |
| KRT6C | GCCCAATACGAGGAGATTGC | CCTCTGGATCATGCGGTTGA | 58 |
| OAS2 | AGGTGGCTCCTATGGACGGAA | GGCTTCTCTTCTGATCCTGGAATTG | 58 |
| IFI44 | TACCAGTTTAATCCCATGGAATCA | CAAATACAAATGCCACACAATGAA | 58 |
| KRT16 | ATGCTTGCTCTGAGAGGTCA | TCTTTGTTCAGCTCCTCGGT | 58 |
| SERPINB2 | CGATTTTGCAGGCACAAGCT | CCTGTGGATGCATTGATTGC | 58 |
| KRT5 | ATCGCCACTTACCGCAAGCTGCTGGAGGG | AAACACTGCTTGTGACAACAGAG | 58 |
| CD24 | CTGGCACTGCTCCTAC | GAGTGAGACCACGAAG | 58 |
| GATA3 | GCCCGGTCCAGCACAGAAGG | AGGGGCCGGTTCTGTCCGTT | 58 |
| FOXA1 | GAAGATGGAAGGGCATGAAA | GCCTGAGTTCATGTTGCTGA | 58 |
| KRT20 | CAGACACACGGTGAACTATGG | GATCAGCTTCCACTGTTAGACG | 58 |
| XBP1 | CCTTGTAGTTGAGAACCAGG | GGGGCTTGGTATATATGTGG | 58 |
| PEG3 | CCAAGAGAAGTGCCTACCCA | TCCCTTGCTCTTCCCGATTT | 58 |
| SOX2 | CCCACCTACAGCATGTCCTACTC | TGGAGTGGGAGGAAGAGGTAAC | 58 |
| ALDH1A1 | TGTTAGCTGATGCCGACTTG | TTCTTAGCCCGCTCAACACT | 58 |
| Bmi1 | CGTGTATTGTTCGTTACCTGGA | TTCAGTAGTGGTCTGGTCTTGT | 58 |
| OCT4 | GTCCGAGTGTGGTTCTGTA | CTCAGTTTGAATGCATGGGA | 58 |
| LGR5 | GATGTTGCTCAGGGTGGACT | TTTCCCGCAAGACGTAACTC | 58 |
| NANOG | CAGCTGTGTGTACTCAATGATAGATTT | ACACCATTGCTATTCTTCGGCCAGTTG | 58 |
| ΔNp63 | ACCTGGAAAACAATGCCCAGA | ACGAGGAGCCGTTCTGAATC | 58 |
| CK14 | GGCCTGCTGAGATCAAAGAC | GTCCACTGTGGCTGTGAGAA | 58 |
| CD133 | TGGGGCTGCTGTTTATTATTCT | TGCCACAAAACCATAGAAGATG | 58 |
| CD44 | AGAAGGTGTGGGCAGAAGAA | AAATGCACCATTTCCTGAGA | 58 |
| CD49f | CGAAACCAAGGTTCTGAGCCCA | CTTGGATCTCCACTGAGGCAGT | 58 |

Sequences of primers for Q-RT-PCR used in the present study

| Gene name | Forward primer (SEQ ID NOS 1-42, respectively, in order of appearance) | Reverse primer (SEQ ID NOS 43-84, respectively, in order of appearance) | Annealing temperatures |
|---|---|---|---|
| CD90 | CGCTCTCCTGCTAACAGTCTT | CAGGCTGAACTCGTACTGGA | 54 |
| FGF2 | CTGGCTATGAAGGAAGATGGA | TGCCCAGTTCGTTTCAGTG | 58 |
| FGFR1 | CGCCCCTGTACCTGGAGATCATCA | TTGGTACCACTCTTCATCTT | 58 |
| ABCG2 | AGCTGCAAGGAAAGATCCAA | TCCAGACACACCACGGATAA | 58 |
| Uroplakin II | CACTGAGTCCAGCAGAGAGATC | ACAGAGAGCAGCACCGTGATGA | 54 |
| Uroplakin IIIA | AGTGTGACTTTCGCCACCAACAAC | ATTCAGGATCTGTGAGGCCTTGGA | 54 |
| COX2 | TCTGCAGAGTTGGAAGCACTCTA | GCCGAGGCTTTTCTACCAGAA | 58 |
| YAP1 | ACCCACAGCTCAGCATCTTCG | TGGCTTGTTCCCATCCATCAG | 58 |
| β-actin | TTCTACAATGAGCTGCGTGTG | GGGGTGTTGAAGGTCTCAAA | 58 |

[a]Quantitative-RT-PCR was done at 50° C. for 2 min, 95° C. for 10 min, followed by 40 cycles at 95° C. for 15 sec and the optimal annealing temperature for 1 min.

Human Stem Cell RT[2] Profile PCR Array

Gene expression profiling using the Human Stem Cell RT[2] Profiler PCR Array (SA Biosciences, Cat # PAHS-405ZA) was conducted in HUC1 cells exposed at different time period of arsenic (6, 8, 10, 12 months), the arsenic exposed HUC1 without arsenic for 2.5 months (As+2.5M UE), the passage-matched UE-cells, 12M As and UE-spheroid cells, and BFTC 905 cell. Real-Time PCR was performed using RT[2] SYBR Green qPCR Mastermix on a 7900HT thermocycler. Each replicate cycle threshold (CT) was normalized to the average CT of 5 endogenous controls per plate basis. The fold change for each arsenic exposed cells relative to the control cells was calculated using the 2-ΔΔCt method.

Gene Expression Profiling

Expression profile on 10M UE, 10M As, 10M As+2.5M UE, and BFTC 905 cells was performed using HumanHT-12 v4 Expression BeadChip (Illumina, San Diego, USA). Total RNA (500 ng per sample) from 10M UE, 10M As, 10M As+2.5M UE, and BFTC 905 cells was amplified into cRNA, which was biotinylated using an Illumina Total Prep RNA amplification kit (Ambion) according to the manufacturer's protocol. The biotinylated cRNA was combined with hybridization buffer and hybridized to HumanHT-12 v4 Expression BeadChip (Illumina, San Diego, USA), including 47,231 probes derived primarily from genes in the NCBI RefSeq database. After washing, the chip was stained with streptavidin-Cy3, and dried chip was protected from light until scanning with an iScan System (illumina). GenomeStudio software (illumina) was used to generate signal intensity values from the scans and perform the initial quality controls. The raw signal intensities of all samples were quantile normalized to the median distribution, and subsequently $\log_2$ transformed. Differentially expressed genes were identified by fitting a linear model. Significant levels (P-values) were adjusted using Benjamini and Hochberg false discovery rate (FDR) method to correct for multiple hypothesis testing. All statistical analyses were performed using lumi and limma package in R software (Bioconductor, Seattle USA).

Gene Set Enrichment Analysis (GSEA) was used to identify gene sets enriched by arsenic exposure in oncogenic signatures or Gene Ontology (GO) biological process from the Molecular Signatures Database (MSigDB; Broad Institute). The nominal P-value estimates the statistical significance of the enrichment score, and FDR<0.25 were considered for the identification of biologically relevant gene sets upon arsenic exposure. Gene sets were ranked based on the normalized enrichment score (NSE) with nominal P-value <0.05. The gene expression data are deposited at the NCBI Gene Expression Omnibus (GEO) database under accession ID GSE90023.

Bisulfite Treatment and Sequencing

Cell pellets were digested with 1% sodium dodecyl sulfate and 50 μg/mL proteinase K (Roche, Nutley, USA) at 48° C. overnight. Isolation of genomic DNA from cell lines was performed with the phenol-chloroform extraction protocol followed by ethanol precipitation. Bisulfite treatment was conducted using an EpiTect Bisulfite Kit (QIAGEN, Valencia, USA), and was subsequently amplified via PCR using primers as shown in the following table. PCR products were purified using the QIAquick Gel Extraction kit (Qiagen), and sequenced by Genewiz DNA sequencing service (Genewiz, South Plainfield, USA). The data were analyzed using the Sequence Scanner v1.0 software (Life technologies). A methylation frequency of ≥50% of total CpG sites within the amplified region was considered "methylation-positive".

For demethylation, cells ($1\times10^6$/T-75 flask) were treated with 1 or 5 mmol/L of the demethylating agent 5-Aza-dC (Sigma) dissolved in 50% acetic acid or were mock-treated with phosphate buffered saline (PBS) including the same amount of acetic acid every 24 hours for 5 days. When combined with the histone deacetylase inhibitor TSA (Sigma), 300 nmol/L TSA was added to the medium for the final 24 hours.

Sequences of primers for bisulfite sequencing used in the present study

| Gene name Bisulfite Sequencing[a] | Forward primer-1 SEQ ID NOS 85-88, respectively, in order of appearance | Forward primer-2 SEQ ID NOS 89-92, respectively, in order of appearance | Reverse primer SEQ ID NOS 93-96, respectively, in order of appearance | Annealing temperatures |
|---|---|---|---|---|
| MIRLET7BHG | GATTTAGGGTGTGGGT TGGGTTAGT | GAAGGAATTTATAGGAGGT GGGGAT | TCACCCACCAAATACTAA AAATCTCCA | 56 |
| MIR200C | GTGGTTAAGTTTTAGA GGAGGTGTT | TAAAGGTTATTAGGGGAGA GGTTTT | ACAACTTCAAACCCAAA ATCCCTAC | 54 |
| MIR296 | TTAGATTAGATATAAA GGTTTTGGAGATTG | AATAATAAATAATAGTTTA AAGATTGTT | CAAATTTAAAATAAAAA CAAAAAAAA | 54 |
| EGFL7 | AGTTATTTTTATTTTT TAGTATTTGT | GTGTTTTGGGTTTTTGTAGT TTTG | CAAAACAACAAACCATA CCAACCTC | 56 |

[a]PCR for bisulfite sequencing was done at 95° C. for 3 min, followed by 40 cycles at 95° C. for 1 min, optmal temperature for 1 min, and 72° C. for 1 min in a 25 μL reaction volume containing 1 μL bisulfite-treated genomic DNA, 2.5 μL 10X PCR Buffer, 1.3 μL dimethyl sulfoxide, 1.5 mmol/L dNTP mixture, 400 nmol/L of each primer, and 0.5 μL Platinum® Taq DNA Polymerase (Invitrogen, Frederick, USA).

Western Blotting Analysis

Whole cell lysates were extracted using RIPA buffer (Thermo Scientific) supplemented with 10 μL/mL Halt™ Protease Inhibitor Cocktail Kit (Life Technologies) and 30 μL/mL Halt™ Phosphatase Inhibitor Cocktail Kit (Life Technologies). The protein concentrations were determined using a Pierce™ BCA Protein Assay Kit (Life Technologies), and the protein were separated on NuPAGE® 4-12% Bis-Tris Gel (Life Technologies) according to the manufacturer's protocol. COX2 (D5H5), NANOG (D73G4), OCT4 (D705Z), CD133 (A3G6K), Snail (C15D3), ZEB1 (D80D3), Vimentin (D21H3), CDH2 (D4R1H), CDH1 (24E10), p-EGFR (D7A5), EGFR (D38B1), p-AKT (D9E), AKT (cat #, 9272), p-ERK (D13.14.4E), ERK (137F5), p-YAP1 (D9W2I), p-Src (cat #, 2101), Src (36D10), DNMT1 (D63A6), DNMT3A (D23G1), and DNMT3B (D7O7O) antibodies were obtained from Cell Signaling Technology (Danvers, Mass., USA), except for SOX2 (EPR3131; Abcam, Cambridge, USA), YAP1 (ab52771; Abcam), CD24 (cat #, AF5247-SP; R&D Systems, Minneapolis USA) and β-actin (A2228; Sigma-Aldrich). Secondary horseradish peroxidase (HRP)-conjugated antibodies were obtained from Cell Signaling Technology, and chemiluminescent detection of HRP-labeled antibodies was performed using Amersham ECL Prime Western Blotting Detection Reagent (GE Healthcare, Piscataway, USA). As loading control, β-actin was used.

Enzyme-Linked Immunosorbent Assay (ELISA)

Cells were cultured in serum-free medium, and PGE2 level in cell culture supernatants after serum starvation or CDDP (5 μM) treatment for 72 hours was measured by quantitative ELISA kits (R&D Systems) according to the manufacturer's protocol. Comprehensive analysis of cytokines was performed by Human Cytokine ELISA plate Array I (Signosis, Santa Clara, USA). YAP1-LV, YAP-LV/SOX2-sh, YAP1-sh, YAP1-sh/SOX2-LV, and YAP1-Ctrl/SOX2-Ctrl cells were culture in serum-free medium for 48 hours, and the cell culture supernatants were used.

Tissue Microarray (TMA) and Immunohistochemical Staining (IHC)

Formalin-fixed paraffin-embedded tissue microarray (TMA) sections were constructed from a total of 528 cores from 243 primary UCB tumors treated at The Johns Hopkins University School of Medicine and the George Washington University. After antigen retrieval was performed with Tris-HCl+ethylenediaminetetraacetic acid (pH 9.0) at 750 W for 20 min in microwave oven, the sections were blocked with 1% bovine serum albumin, followed by incubation with the following primary antibodies overnight at 4° C.: SOX2 (1:100; Abcam), COX2 (1:500; Cell Signaling Technology), YAP1 (1:300; Abcam), EP4 (1:100; Abcam), FOXP3 (1:250; eBioscience, San Diego, USA), and CD8 (1:900, Thermo Scientific). Hydrogen peroxide, serum biotinylated immunoglobulins, and avidin-biotin complexes were used according to the manufacturer's instructions (Dako, Golstrup, Denmark). After induction of the color reaction with freshly made diaminobenzidine solution (Dako), slides were counterstained with hematoxylin. BFTC905 and J82 cells were used as positive and negative control, respectively. Immunohistochemical staining was scored by a urologic pathologist. For transcription factors YAP1 and SOX2 nuclear staining was considered while cytoplasmic staining was scored for COX2 and EP4. An intensity score (0-3+) and an extent score (percentage; 0-100) were assigned in each spot. For each spot, intensity and extent of staining were multiplied for a staining score (score range 0-300) by light microscopy for COX2, SOX2, YAP1, and EP4. A cutoff score of >50 was defined as positive expression (13) {Orbo, 2016 #47}. We previously assessed the number of FOXP3- and/or CD8-positive tumor-infiltrating lymphocytes (TILs) per high power filed (HPF) in several TMA sections (14). We assessed the correlation between YAP1/COX2/SOX2 and FOXP3- or CD8-positive TILs in each tumor in serial levels of the same TMA sections.

TCGA Analysis

The gene expression data of 408 TCGA primary UCB samples were downloaded from the Broad GDAC Firehose (http://gdac.broadinstitute.org/), which is the RSEM transcripts per million (TPM) estimates and subsequently transformed as the $\log_2$ TPM data. A group of 35 MDSC-related genes that have been linked to immunosuppressive signature were used to perform Ward hierarchical clustering on the Manhattan distance, which categorized 408 TCGA UCB samples into three groups: MDSC-high, MDSC-medium, and MDSC-low (15) (16). The expression of YAP1, COX2, and SOX2 in MDSC-high group was compared with MDSC-low group using the Wilcoxon test.

Gene Silencing and Expression

SOX2 or YAP1 shRNA pGFP-C-shLenti Vector (SOX2-sh or YAP1-sh) was used for knockdown of the gene expression (Origene, Rockville, USA; Cat # TL309173 and TL308332). Lentiviral particles were produced by cotransfection of each lentiviral vector with the Lenti-vpak Packaging Kit (Origene) into 293 cells according to the manufacturer's protocol. Cells were seeded in 6-well plates (2×105 cells per well) for transduction. After 24 hours, lentiviral particles were added to the cells in the presence of 8 mg/mL polybrene (EMD Millipore) and incubated at 37° C. for 4 hours. The medium was then replaced with fresh medium. Non-effective 29-mer scrambled shRNA pGFP-C-shLenti Vector (Origene; Cat # TR30021) was used as control (SOX2- or YAP1-Ctrl). EF1A-Human-SOX2 lentivirus (SOX2-LV) for SOX2 induction, LentimiRa-GFP-has-let-7 lentivirus (let-7-LV) for let-7 induction, and YAP1 inducible lentivirus (YAP1-LV) for YAP1 induction were purchased from Cellomics Technology (Rockville, USA; Cat # PLV-10013), Applied Biological Materials (Richmond, Canada; Cat # mh15004) and GenTarget (San Diego, USA; Cat # LVP478), respectively. EF1A-vector control lentivirus (Cat # PLV-10074), Lenti-III-mir-GFP control lentivirus (Cat # m002), and CMV control lentivirus (Cat # CMV-Null-RB) were used as control, respectively. Stable cells were established by optimal antibiotic selection. To establish stable cells with YAP1 silencing and SOX2 overexpression, YAP1-sh cells were transduced with SOX2 lentivirus (YAP1-sh/SOX2-LV), and each single cell was plated in 96 wells. Western blotting analysis was performed to confirm stable YAP1 silencing and SOX2 overexpression after screening the expression level of each clone using Q-RT-PCR. Stable cells with YAP1 overexpression and SOX2 silencing (YAP1-LV/SOX2-sh) also were established by the same method. For knockdown of COX2, cells were transfected with COX-2 Silencer Select siRNA (Thermo Fisher Scientific; Cat # s11472) at the final concentration of 10 nM by forward transfection using Lipofectamine RNAiMAX (Invitrogen) according to the manufacturer's protocol. Silencer Select Negative Control No. 1 siRNA (Thermo Fisher Scientific; Cat #4390843) was used as control for nonspecific effects. To verify the knockdown, western blotting analysis was performed 72 hours after transfection.

Flow Cytometric Analysis

For extracellular staining, cells (1×10$^6$/100 μL stain buffer) were incubated with PE-Vio770-conjugated anti-human CD133 (293C3; Miltenyi Biotec, Auburn, USA) or PE-conjugated anti-human CD24 antibody (cat #, 560991; BD Biosciences) for 30 min at 4° C. in dark. PE-Vio770-conjugated Isotype (cat #, 130-098-563; Miltenyi Biotec) and PE-conjugated IgG2a, κ Isotype (cat #, 555574; BD Biosciences) were used as control for CD133 and CD24 staining, respectively. Staining for intracellular SOX2 was carried out using the BD Cytofix/Cytoperm Fixation/Permeabilization Kit (BD Biosciences) according to manufacturer's protocol. The cells were incubated with Alexa Fluor 647-conjugated anti-SOX2 antibody (cat #, 560302; BD Biosciences) for 40 min at 4° C. in dark. Alexa Fluor 647-conjugated anti-IgG2a, κ Isotype (cat #, 558053; BD Biosciences) was used as control. Data were acquired on a BD FACSCalibur flow cytometer (BD Biosciences) using BD CellQuest Pro software (BD Biosciences) and analyzed with FlowJo software v10.1 (Tree Star, Ashland, USA).

For apoptosis assay, cells were exposed to CDDP (5 or 10 μM) for 72 hours under serum-free medium and stained with PE Annexin V and 7-AAD for discrimination of early and late apoptosis using the PE Annexin V Apoptosis Detection Kit I (BD Biosciences).

Magnetic-Activated Cell Sorting

Cells (1×10$^8$) were labelled with PE-conjugated anti-human CD24 antibody (Miltenyi Biotec, Auburn, USA), and subsequently labelled with Anti-PE MultiSort MicroBeads (Miltenyi Biotech). After washing, Magnetic-Activated Cell Sorting for CD24 was performed using MACS Columns and MidiMACS Separator (Miltenyi Biotec). Next, both CD24 negative and positive fraction were labelled with CD133 MACS MicroBeads (Miltenyi Biotec), followed by sorting using MACS Columns and MidiMACS separators. This process leaded to the separation of CD24$^-$/CD133$^-$, CD24$^-$/CD133$^+$, CD24$^+$/CD133$^-$ and CD24$^+$/CD133$^+$ enriched cell population. To confirm the separation, flow cytometric analysis was carried out using PE-conjugated anti-human CD24 antibody (Miltenyi Biotec) and PE-Vio770-conjugated anti-human CD133/2 (Miltenyi Biotec). PE-conjugated anti-IgG1K Isotype (Miltenyi Biotec) and PE-Vio770 conjugated IgG2b Isotype (BD Biosciences) were used as control for CD24 and CD133 staining, respectively.

Cell Proliferation and Viability Assay (MTT Assay)

The cell proliferative and viability activity were measured using the 3-(4, 5-dimethyl thiazol-2-yl)-2, 5-diphenyltetrazolium bromide (MTT) Proliferation Assay Kit (ATCC; Manassas, Va., USA) according to the manufacturer's protocol. Cells were seeded in a 96-well plate at a density of 5×10$^3$ per well and incubated at 37° C. until the indicated time points. At the end of each time point, 10 μL MTT Reagent was added to the culture medium, which was then incubated in the dark for a further 4 hours at 37° C. This step was followed by cell lysis with the addition of 100 μL Detergent Reagent. The plates were incubated for 2 hours at 37° C. to dissolve formazan crystals. Spectrophotometric readings (570 nm-650 nm) were obtained on a Spectra Max 250 96-well plate reader (Molecular devices, Sunnyvale, USA). Spheroid cells were cultured in ultra-low attachment 96 well plates under serum-free condition. Cell viability was expressed as the ratio of absorbance values of the treated cells related to the untreated control cells considered as 1.0. The half maximal (50%) inhibitory concentration (IC$_{50}$) value of drug was calculated by treatment with the various concentration for 72 hours using MTT assay. Each assay was performed in triplicate, and each experiment was repeated at least three times.

Invasion Assay and Wound Healing Assay

The invasion assay was performed using the 24-well BD BioCoat Matrigel Invasion Chamber (BD Biosciences). The lower chamber was filled with 750 μL DMEM supplemented with 10% FBS as a chemoattractant, and cells (5×10$^4$/well) were then seeded into an upper chamber in 500 μL of serum-free DMEM. After incubation for 48 hours, the membrane of the upper chamber was fixed and stained using Hemacolor Stain Set (EMD Millipore, Billerica, USA). Cells that had invaded through the membrane were counted under a microscope in 10 randomly selected fields (magnification ×20) per well and averaged. To normalize for cell invasion differences, each cell line was also grown on an uncoated insert. Number of invaded cells was divided by the number of cell counted on the uncoated inserts.

For wound healing Assay, cells (5×10$^4$) were seeded into each well of Culture-Inserts (ibidi, Verona, USA) on 6 well plates, and incubated at 37° C. for 24 hours. The Culture Insert was gently removed using sterile tweezers, and a 500-μm wide cell-free gap (wound) was generated. The used plates was then filled with 2 mL of cell-free medium. The monolayer was imaged at time points to record the size of the wound until closure of the wound. The area of wound coverage was calculated using NIS-Elements Microscope Imaging Software (Nikon Instruments, Melville, USA) and normalized by the zero time point area. Quantification of cell motility was evaluated by measuring the wound coverage for each time point. The degree of motility was expressed as the percentage of wound closure compared with the zero time point. Both experiments were carried out in triplicate.

Sphere Formation Assay and Self-Renewal Assay

Sphere formation was induced by culturing cells ($2\times10^4$/well) in DMEM/Ham's F12 50/50 Mix (Mediatech) supplemented with B-27 (Life Technologies), 20 ng/mL FGF-basic (Peprotech), 20 ng/mL EGF (Peprotech). Cell culture was performed in ultra-low attachment 6 well plates (Corning, Lowell, USA) for 10 days. The medium was replaced every other day. Sphere formation was evaluated using the inverted phase-contrast microscope, and single sphere with a diameter larger than 100 μm was counted using NIS-Elements Microscope Imaging Software. To redifferentiate spheres, spheres were plated in standard growth medium with 10% FBS in dishes supporting cell attachment, and incubated for 7 days.

For self-renewal assay, primary spheres were collected by gentle centrifugation (5 min at 400×g), dissociated with Stempro Accutase Cell Dissociation Reagent (Life Technologies), and mechanically disrupted with a pipette. The cell suspension was sieved through 40 μm cell strainer cap filter to achieve a single-cell suspension, and then equal numbers of alive cells were plated in ultralow attachment plates to generate the second spheres. Again, spheres were counted on day 14 and digested to generate the third Spheres. All the experiments were performed in triplicate and repeated at least three times.

In Vivo Xenograft Assay and Treatment

Preserved patient-derived tumor xenograft (PDX) tissues (CTG1388 and CTG1061) were obtained from Champion Oncology (Maryland, USA). CTG1388 and CTG1061 PDX tissues were established from primary and metastatic sites of UCB patients, respectively. S16-4522 PDX was established from metastatic lymph node of UCB patient who underwent surgery at Johns Hopkins University. The tumor tissues were subdivided into 4×2 mm size, and embedded within the subcutaneous space underneath the skin of 4-5 week-old NOD/SCID/IL2Rγ−/− (NSG) mice. NSG mice were bred and maintained in the Johns Hopkins Medical Institutes animal care facility.

For tumor formation assay, cells were suspended in 100 μL of a 1:1 mixture of serum-free DMEM and Cultrex Stem Cell Qualified Reduced Growth Factor Basement Membrane Extract (Trevigen, Gaithersburg, USA), and then injected subcutaneously into the both flanks of 4-5 week-old athymic (nu+/nu+) mice (Harlan Laboratories, Indianapolis, USA) for BFTC905, BFTC909, and SCaBER cells, or NSG mice for T24 and 5637 cells. Mice were maintained under pathogen-free conditions within the institutional animal facility, and randomly assigned to groups (four mice per group). Tumor growth was monitored every three days, and tumor volume was calculated from caliper measurements of two orthogonal diameters [larger (x)] and smaller (y) diameters] using the following formula: volume=$xy^2/2$. At the end of experiments, mice were euthanized and tumors were dissected and weighted. The dissected tumors were homogenized for RNA or protein extraction. For limiting dilution assay, spheroid cells or CD24/CD133 sub-populated cells were serially diluted ($1\times10^5$, $1\times10^4$, $1\times10^3$, or $1\times10^2$ cells per flank) and subcutaneously injected into the both flanks of NSG mice. The mice were euthanized when tumor reached 2 cm in diameter, or 20 weeks later. Tumor-forming rates (the numbers of tumors/the number of injections) were numerated to calculate the tumor-initiating capacity.

For therapeutic efficacy, mice were randomly assigned into experimental groups (five mice per group) when tumors reached a volume of 100-200 mm$^2$. For celecoxib and/or VP treatment, celecoxib (5 mg/kg) was administered via intraperitoneal (i.p.) injection once a day (17), and VP (50 mg/kg) was administered via i.p. every other day (18). EP4 antagonist ONO-AE3-208 (10 mg/kg) was administered via i.p. once a day (19). Control was applied with same volume (100 μL per injection) of 10% dimethyl sulphoxide in 1 TWEEN 80 (Sigma-Aldrich). For GEM and CDDP (GC) treatment (i.p.), CDDP (6 mg/kg) was only applied after the first GEM (60 mg/kg) treatment on day 2, followed by three consecutive treatments of GEM on day 5, 8 and 11 (17). The next cycle was started on day 18, and the treatment was continued until tumor reached 2 cm in diameter. For erlotinib treatment, the mice were treated once a day, 6 days per week, by oral gavage with erlotinib (100 mg/kg) or control (PBS containing 0.5% methyl cellulose (Sigma-Aldrich) and 0.1% TWEEN 80) (20). Tumor size was measured at least every three days. Therapeutic efficacy was assessed using percentage change after treatment related to tumor size before treatment. To establish xenograft model with acquired resistance to erlotinib, erlotinib sensitive 5637 cells were injected subcutaneously into the both flanks of 4-5 week-old NSG mice, and the tumors were consecutively passaged from NSG mice treated with erlotinib and celecoxib until the development of refractory tumors. All experiments using mice were approved by the Johns Hopkins University Animal Care and Use Committee, and the mice were maintained in accordance with the American Association of Laboratory Animal Care guidelines.

All experiments using mice were approved by the Johns Hopkins University Animal Care and Use Committee, and the mice were maintained in accordance with the American Association of Laboratory Animal Care guidelines. Informed consent was obtained from the patients before sample collection. Approval for research on human subjects was obtained from the Johns Hopkins University institutional review boards. This study qualified for exemption under the U.S. Department of Health and Human Services policy for protection of human subjects [45 CFR 46.101(b)]

Statistical Analysis

In each set of data analysis, estimate variation is indicated in each figure as standard error of mean (SEM). A comparison between the two groups was performed with two-tailed student's t-test or Wilcoxon-Mann-Whitney test where appropriate. A comparisons between the multiple groups were performed with Kruskal-Wallis with post-hoc test (Dwass-Steel test) for non-parametrically continuous variables and ANOVA with Tukey's post hoc test for parametrically continuous variables. Categorical variables were analyzed using Fisher's exact test or the chi-square test. No statistical method was used to predetermine sample size. The level of statistical significance was set at P<0.05. All statistical analyses were conducted with JMP 12 software package (SAS Institute, Cary, USA).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating cancer in a subject in need thereof comprising administering to the subject an effective amount of a cyclooxygenase-2 (COX 2) inhibitor and a yes-associated protein 1 (YAP 1) inhibitor and wherein the cancer is selected from the group consisting of bladder cancer and urothelial carcinoma.

2. The method of claim 1 wherein the COX 2 inhibitor is celecoxib or a pharmaceutically acceptable salt, solvate, or stereoisomer thereof.

3. The method of claim 1 wherein the YAP1 inhibitor is verteporfin, or a pharmaceutically acceptable salt, solvate, or stereoisomer thereof.

4. The method of claim 1 wherein the subject is also administered one or more other chemotherapy agents.

5. A method for treating cancer in a subject in need thereof comprising administering to the subject an effective amount of a celecoxib, or pharmaceutically acceptable salt, solvate, or stereoisomer thereof, and an effective amount of verteporfin, or pharmaceutically acceptable salt, solvate, or stereoisomer thereof, and wherein the cancer is selected from the group consisting of bladder cancer and urothelial carcinoma.

6. The method of claim 5 wherein the subject is also administered one or more other chemotherapy agents.

7. A method of enhancing a chemotherapeutic response in a subject having cancer comprising the following steps:
   a) administering an effective amount of COX2 inhibitor to the subject;
   b) administering an effective amount of YAP1 inhibitor to the subject;
   c) administering an effective amount of a chemotherapy agent to the subject,
      wherein the cancer is selected from the group consisting of bladder cancer and urothelial carcinoma.

8. The method of claim 7 wherein the cancer patient is administered an effective amount of COX2 inhibitor and YAP1 inhibitor prior to the administering the chemotherapy agent.

9. The method of claim 7 wherein the cancer patient is administered an effective amount of chemotherapy agent prior to the administering of COX 2 inhibitor.

10. The method of claim 7 wherein the COX 2 inhibitor is celecoxib or a pharmaceutically acceptable salt, solvate, or stereoisomer thereof.

11. The method of claim 7 wherein the YAP1 inhibitor is verteporfin, or a pharmaceutically acceptable salt, solvate, or stereoisomer thereof.

12. A method for treating cancer in a subject in need thereof comprising administering to the subject an effective amount of a EP4 antagonist and an effective amount of a COX2 inhibitor and wherein the cancer is selected from the group consisting of bladder cancer and urothelial carcinoma.

13. The method of claim 12 wherein the COX2 inhibitor is etodolac.

14. A method for treating cancer in a subject in need thereof comprising administering to the subject an effective amount of a EGFR inhibitor an effective amount of a COX 2 inhibitor and an effective amount of a YAP 1 inhibitor, and wherein the cancer is selected from the group consisting of bladder cancer and urothelial carcinoma.

15. The method of claim 14 wherein the subject is administered a YAP1 inhibitor in addition to the EGFR inhibitor and the COX 2 inhibitor.

16. The method of claim 4, wherein the one or more chemotherapy agents comprise gemcitabine or cisplatin.

17. The method of claim 6, wherein the one or more chemotherapy agents comprise gemcitabine or cisplatin.

18. The method of claim 7, wherein the one or more chemotherapy agents comprise gemcitabine or cisplatin.

19. The method of claim 12, wherein the EP4 antagonist is ONO-AE3-208.

20. The method of claim 14, wherein the method further comprises administering to the subject one or more chemotherapy agents comprising gemcitabine and/or cisplatin.

21. The method of claim 14 wherein the COX 2 inhibitor is celecoxib or a pharmaceutically acceptable salt, solvate, or stereoisomer thereof.

22. The method of claim 14 wherein the YAP1 inhibitor is verteporfin, or a pharmaceutically acceptable salt, solvate, or stereoisomer thereof.

23. A method for EGFR inhibitor resistant bladder cancer or urothelial carcinoma cancer in a subject in need thereof comprising administering to the subject an effective amount of a an effective amount of a COX 2 inhibitor and an effective amount of a YAP 1 inhibitor.

24. The method of claim 23 wherein the COX 2 inhibitor is celecoxib or a pharmaceutically acceptable salt, solvate, or stereoisomer thereof.

25. The method of claim 23 wherein the YAP1 inhibitor is verteporfin, or a pharmaceutically acceptable salt, solvate, or stereoisomer thereof.

26. The method of claim 23 wherein the subject is also administered one or more other chemotherapy agents.

27. The method of claim 26, wherein the one or more chemotherapy agents comprise gemcitabine or cisplatin.

28. The method of claim 26, wherein the one or more chemotherapy agents comprises an EGFR inhibitor.

* * * * *

```
                        SEQUENCE LISTING

<160> NUMBER OF SEQ ID NOS: 97

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agagtgcaaa tgcacctcct gc                                              22

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcgccatgga tcccaactg                                                  19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccccagattc aggatcagac agcc                                            24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgggccaaag gatgaagaga                                                 20

<210> SEQ ID NO 5
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 5
tggaagacac cctaatgtg                                                    19

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaccagtgga tctgccaact actc                                              24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaggaggtgg aggctttgat c                                                 21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtggctgttg agcgaataac tg                                                22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agagctggaa ggaggaggtg                                                   20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
actttccact ggctctcaaa ctct                                              24

<210> SEQ ID NO 11
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 11
gcccaatacg aggagattgc                                                   20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aggtggctcc tatggacgga a                                                 21

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taccagttta atcccatgga atca                                              24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgcttgctc tgagaggtca                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgattttgca ggcacaagct                                                   20

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atcgccactt accgcaagct gctggaggg                                         29

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic

```
                                      primer

<400> SEQUENCE: 17
ctggcactgc tcctac                                                        16

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcccggtcca gcacagaagg                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaagatggaa gggcatgaaa                                                    20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagacacacg gtgaactatg g                                                  21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccttgtagtt gagaaccagg                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccaagagaag tgcctaccca                                                    20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 23
cccacctaca gcatgtccta ctc                                          23

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgttagctga tgccgacttg                                              20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgtgtattgt tcgttacctg ga                                           22

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtccgagtgt ggttctgta                                               19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gatgttgctc agggtggact                                              20

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagctgtgtg tactcaatga tagattt                                      27

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 29
acctggaaaa caatgcccag a                                              21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggcctgctga gatcaaagac                                                20

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tggggctgct gtttattatt ct                                             22

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agaaggtgtg ggcagaagaa                                                20

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgaaaccaag gttctgagcc ca                                             22

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgctctcctg ctaacagtct t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
```

```
ctggctatga aggaagatgg a                                              21
```

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
cgcccctgta cctggagatc atca                                           24
```

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
agctgcaagg aaagatccaa                                                20
```

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
cactgagtcc agcagagaga tc                                             22
```

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
agtgtgactt tcgccaccaa caac                                           24
```

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
tctgcagagt tggaagcact cta                                            23
```

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acccacagct cagcatcttc g                                        21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttctacaatg agctgcgtgt g                                        21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cggacatcag gcacagcagc t                                        21

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aggtttgtgg aagtcgcgt                                           19

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgggactatt aggctcaggt gaac                                     24

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cacatcggcc acaccatc                                            18

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggccgtgtca acaaggatac tt                                       22

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ctgcgccaaa agctgcat                           18

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
aagtagggcc caaaggtctt g                       21

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
gcctttgctg ggccaat                            17

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
aggtctccgt cctggaactt                         20

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
atacaggctt tgtacatcat aggactagt                29

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
cctctggatc atgcggttga                         20

```
<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggcttctctt ctgatcctgg aattg                                          25

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caaatacaaa tgccacacaa tgaa                                           24

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tctttgttca gctcctcggt                                                20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cctgtggatg cattgattgc                                                20

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aaacactgct tgtgacaaca gag                                            23

<210> SEQ ID NO 59
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gagtgagacc acgaag                                                    16
```

```
<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aggggccggt tctgtccgtt                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcctgagttc atgttgctga                                              20

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gatcagcttc cactgttaga cg                                           22

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggggcttggt atatatgtgg                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tcccttgctc ttcccgattt                                              20

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tggagtggga ggaagaggta ac                                           22

<210> SEQ ID NO 66
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ttcttagccc gctcaacact                                                    20

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ttcagtagtg gtctggtctt gt                                                 22

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctcagtttga atgcatggga                                                    20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tttcccgcaa gacgtaactc                                                    20

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
acaccattgc tattcttcgg ccagttg                                            27

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acgaggagcc gttctgaatc                                                    20

<210> SEQ ID NO 72
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtccactgtg gctgtgagaa                                              20

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tgccacaaaa ccatagaaga tg                                           22

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aaatgcacca tttcctgaga                                              20

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cttggatctc cactgaggca gt                                           22

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
caggctgaac tcgtactgga                                              20

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgcccagttc gtttcagtg                                               19

<210> SEQ ID NO 78
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 78
ttggtaccac tcttcatctt                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tccagacaca ccacggataa                                              20

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
acagagagca gcaccgtgat ga                                           22

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
attcaggatc tgtgaggcct tgga                                         24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gccgaggctt ttctaccaga a                                            21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tggcttgttc ccatccatca g                                            21

<210> SEQ ID NO 84
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 84
ggggtgttga aggtctcaaa                                                      20

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gatttagggt gtgggttggg ttagt                                                25

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gtggttaagt tttagaggag gtgtt                                                25

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ttagattaga tataaaggtt ttggagattg                                           30

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agttattttt tattttttag tatttgt                                              27

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaaggaattt ataggaggtg gggat                                                25

<210> SEQ ID NO 90
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 90
taaaggttat tagggagag gtttt                                          25

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aataataaat aatagtttaa agattgtt                                      28

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gtgttttggg ttttttgtagt tttg                                         24

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tcacccacca aatactaaaa atctcca                                       27

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
acaacttcaa acccaaaatc cctac                                         25

<210> SEQ ID NO 95
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
caaatttaaa ataaaaacaa aaaaaa                                        26

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
      primer

<400> SEQUENCE: 96
caaaacaaca aaccatacca acctc                                          25

<210> SEQ ID NO 97
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
agcggatgtt ttttaaagtt tgtgtggttg tatttggaag tttgggtggt gtggagacgg    60
cgt                                                                  63
```